United States Patent
Koyanagi et al.

(10) Patent No.: US 8,115,006 B2
(45) Date of Patent: Feb. 14, 2012

(54) PROCESS FOR PRODUCING ANTHRANILAMIDE COMPOUND

(75) Inventors: Toru Koyanagi, Kusatsu (JP); Kazuhiro Yamamoto, Kusatsu (JP); Tetsuo Yoneda, Kusatsu (JP); Shigehisa Kanbayashi, Kusatsu (JP); Toyoshi Tanimura, Kusatsu (JP); Yohei Taguchi, Kusatsu (JP); Tatsunori Yoshida, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 345 days.

(21) Appl. No.: 12/519,177

(22) PCT Filed: Dec. 14, 2007

(86) PCT No.: PCT/JP2007/074169
§ 371 (c)(1),
(2), (4) Date: Jun. 15, 2009

(87) PCT Pub. No.: WO2008/072745
PCT Pub. Date: Jun. 19, 2008

(65) Prior Publication Data
US 2010/0063293 A1 Mar. 11, 2010

(30) Foreign Application Priority Data

Dec. 15, 2006 (JP) .................... 2006-339100
Jun. 8, 2007 (JP) .................... 2007-152718

(51) Int. Cl.
C07D 401/04 (2006.01)
(52) U.S. Cl. .................... 546/275.4
(58) Field of Classification Search .................. 546/275.4
See application file for complete search history.

(56) References Cited

U.S. PATENT DOCUMENTS

| | | | |
|---|---|---|---|
| 4,614,746 A | 9/1986 | Asato et al. |
| 4,820,835 A | 4/1989 | Burger et al. |
| 5,068,392 A | 11/1991 | McKendry et al. |
| 5,998,620 A | 12/1999 | Chen et al. |
| 6,965,032 B2 | 11/2005 | Freudenberger et al. |
| 7,038,057 B2 | 5/2006 | Annis et al. |
| 7,199,138 B2 | 4/2007 | Finkelstein et al. |
| 7,227,025 B2 | 6/2007 | Freudenberger et al. |
| 7,232,836 B2 | 6/2007 | Lahm et al. |
| 2004/0198984 A1 | 10/2004 | Lahm et al. |
| 2005/0075372 A1 | 4/2005 | Lahm et al. |
| 2005/0215798 A1 | 9/2005 | Annis |
| 2006/0128965 A1 | 6/2006 | Annis et al. |
| 2007/0129407 A1 | 6/2007 | Koyanagi et al. |

FOREIGN PATENT DOCUMENTS

| | | |
|---|---|---|
| JP | 61 227557 | 10/1986 |
| JP | 4 334352 | 11/1992 |
| JP | 2004 538327 | 12/2004 |
| JP | 2004 538328 | 12/2004 |
| JP | 2005 502658 | 1/2005 |
| JP | 2005 503384 | 2/2005 |
| JP | 2005 507873 | 3/2005 |
| JP | 2005 534685 | 11/2005 |
| JP | 2006 517592 | 7/2006 |
| WO | 2004 011453 | 2/2004 |
| WO | 2005 077934 | 8/2005 |

OTHER PUBLICATIONS

U.S. Appl. No. 12/516,649, filed May 28, 2009, Koyanagi, et al.
Registry No. 219689-55-1, "Benzamide, 2-amino-5-chloro-N-(cyclopropylmethyl)", URL: https://stnweb-japan.cas.org, pp. 1-3, (2008).
Balasubramaniyan, V. et al., "Reactions of Cyclic Anhydrides: Part XII A Facile Approach to 3,1-Benzoxazin-4-ones via Anilic Acids", Indian Journal of Chemistry, vol. 26B, No. 5, pp. 476-477, (1987).
Martin Vogel et al., "Small-Ring Compounds. XLVII. Reactions of Optically active Cyclopropylmethylcarbinyl Derivatives", Journal of the American Chemical Society, vol. 88, No. 10, pp. 2262-2271, (1966).
Kelley, James L. et al., "6-(Alkylamino)-9-alkylpurines. A New Class of Potential Antipsychotic Agents", J. Med. Chem., vol. 40, No. 20, pp. 3207-3216, (1997).
Ho, Bin et al., "Synthesis and structure-activity relationships of potential anticonvulsants based on 2-piperidinecarboxylic acid and related pharmacophores", Eur. J. Med. Chem., vol. 36, pp. 265-286, (2001).

*Primary Examiner* — Patricia Morris
(74) *Attorney, Agent, or Firm* — Oblon, Spivak, McClelland, Maier & Neustadt, L.L.P.

(57) ABSTRACT

To provide a process for producing a specific anthranilamide compound or its salt.
To provide a process for producing an anthranilamide compound represented by the formula (I) or its salt:

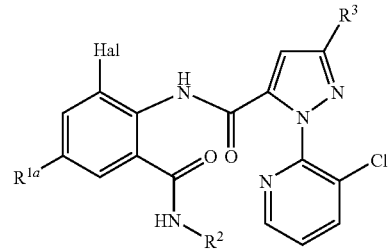

wherein each of $R^{1a}$ and $R^3$ which are independent of each other, is halogen or haloalkyl; $R^2$ is cyclopropyl alkyl or cyclobutyl alkyl; and Hal is a chlorine atom or a bromine atom, which comprises a step of selectively halogenating a compound represented by the formula (II):

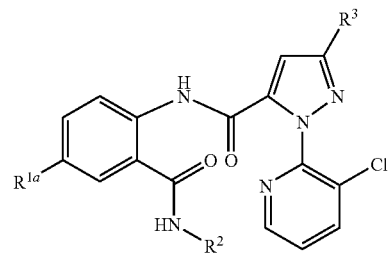

wherein $R^{1a}$, $R^2$ and $R^3$ are as defined above.

3 Claims, No Drawings

PROCESS FOR PRODUCING ANTHRANILAMIDE COMPOUND

TECHNICAL FIELD

The present invention relates to a process for producing an anthranilamide compound.

BACKGROUND ART

With respect to anthranilamide compounds, their excellent effects as pesticides in agricultural and horticultural fields are disclosed, for example, in Patent Document 1. Further, Patent Documents 2 and 3 disclose a process for producing a specific anthranilamide compound.

Patent Document 1: International Publication WO 2005/077934
Patent Document 2: International Publication WO 2003/016283
Patent Document 3: International Publication WO 2004/011453

DISCLOSURE OF THE INVENTION

Object to be Accomplished by the Invention

Heretofore, various processes have been proposed as a process for producing an anthranilamide compound, and a process for producing an anthranilamide compound having a specific substituent pattern of the after-mentioned formula (I) or its salt more efficiently at a low cost has been desired.

Means to Accomplish the Object

The present inventors have conducted extensive studies to accomplish the above object and as a result, found that an anthranilamide compound represented by the formula (I) or its salt can be produced in high yield by selective halogenation of a compound represented by the formula (II) and further found a process capable of efficiently producing a compound of the formula (II-1) as one of the materials thereof, and accomplished the present invention. Namely, the present invention relates to a process for producing an anthranilamide compound represented by the formula (I) or its salt:

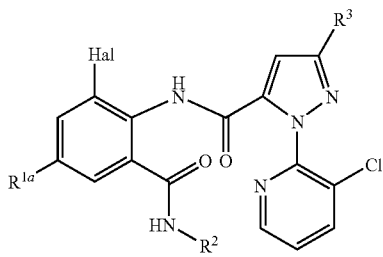

wherein each of $R^{1a}$ and $R^3$ which are independent of each other, is halogen or haloalkyl; $R^2$ is cyclopropyl alkyl or cyclobutyl alkyl; and Hal is a chlorine atom or a bromine atom, which comprises reacting a compound represented by the formula (II):

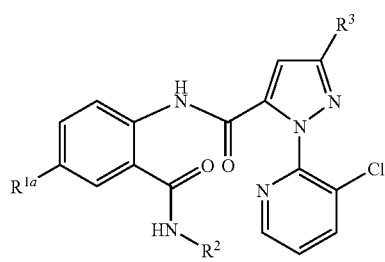

wherein $R^{1a}$, $R^2$ and $R^3$ are as defined above, with a halogenating agent. Further, the present invention relates to a process for producing a compound of the formula (I-1):

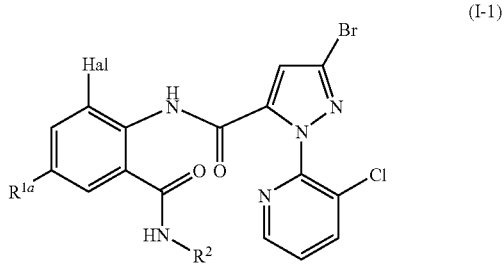

wherein $R^{1a}$, $R^2$ and Hal are as defined above, which is the compound of the above formula (I) wherein $R^3$ is a bromine atom, which comprises reacting a compound represented by the formula (II-1):

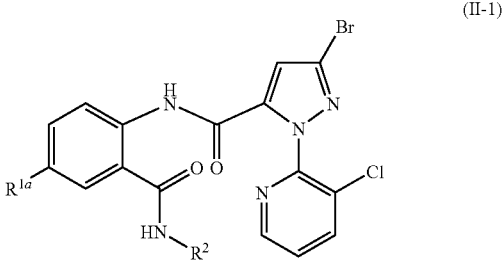

wherein $R^{1a}$ and $R^2$ are as defined above, with a halogenating agent.

Further, the present invention relates to the above process for producing a compound of the formula (I-1), wherein a compound of the formula (II-1), obtained by reacting a compound represented by the formula (III-1):

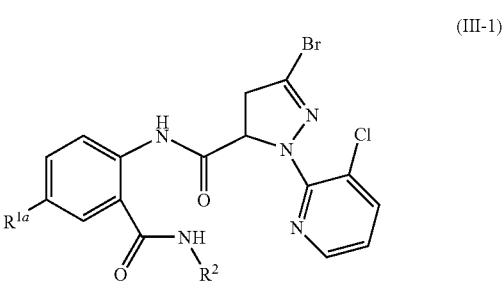

wherein $R^{1a}$ and $R^2$ are as defined above, with an oxidizing agent, or reacting a compound represented by the formula (IV-1):

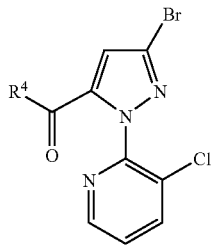
(IV-1)

wherein $R^4$ is $C_{5-10}$ alkyloxy, substitutable phenoxy, substitutable benzyloxy, alkylthio, substitutable phenylthio or substitutable benzylthio, with a compound represented by the formula (V-1):

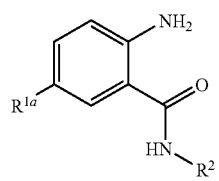
(V-1)

wherein $R^{1a}$ and $R^2$ are as defined above, is reacted with a halogenating agent. Further, the present invention relates to a process for producing a compound represented by the formula (II-1), which is a material for the above reaction:

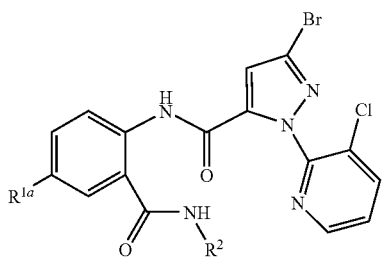
(II-1)

wherein $R^{1a}$ and $R^2$ are as defined above, which comprises reacting a compound represented by the formula (VI-1):

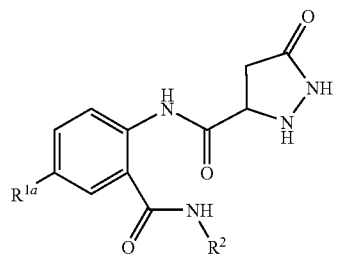
(VI-1)

wherein $R^{1a}$ and $R^2$ are as defined above, with a compound represented by the formula (VII):

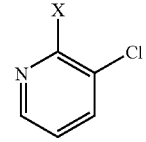
(VII)

wherein X is a chlorine atom or a bromine atom to produce a compound represented by the formula (VIII-1):

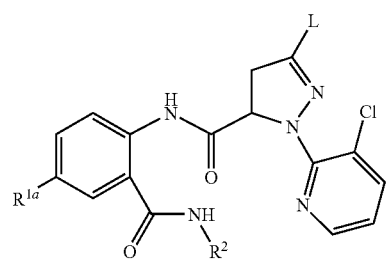
(VIII-1)

wherein $R^{1a}$ and $R^2$ are as defined above, reacting the obtained compound of the formula (VIII-1) with a sulfonyl chloride, a chlorinating agent or an acid chloride to produce a compound represented by the formula (IX-1):

(IX-1)

wherein L is alkylsulfonyloxy, alkoxycarbonyloxy, alkylcarbonyloxy, phenylsulfonyloxy, p-toluenesulfonyloxy or a chlorine atom; and $R^{1a}$ and $R^2$ are as defined above, reacting the obtained compound of the formula (IX-1) with a brominating agent to produce a compound represented by the formula (III-1):

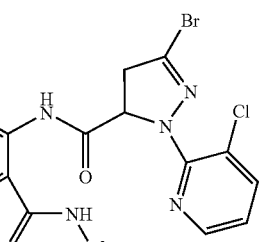
(III-1)

wherein $R^{1a}$ and $R^2$ are as defined above, and reacting the obtained compound of the formula (III-1) with an oxidizing agent.

Still further, the present invention relates to a compound represented by the formula (II-1) or its salt:

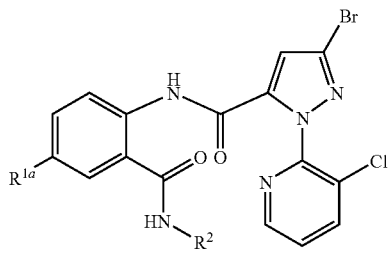

(II-1)

wherein $R^{1a}$ and $R^2$ are as defined above, a compound represented by the formula (V-1) or its salt:

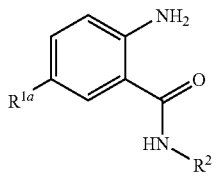

(V-1)

wherein $R^{1a}$ and $R^2$ are as defined above, a compound represented by the formula (VI-1) or its salt:

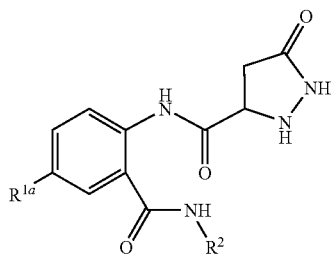

(VI-1)

wherein $R^{1a}$ and $R^2$ are as defined above, a compound represented by the formula (VIII-1) or its salt:

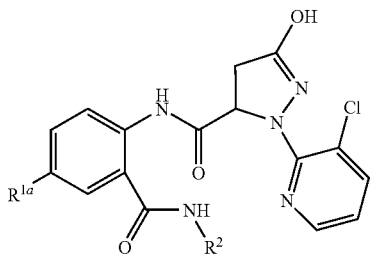

(VIII-1)

wherein $R^{1a}$ and $R^2$ are as defined above, a compound represented by the formula (IX-1) or its salt:

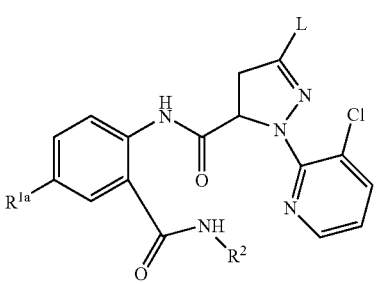

(IX-1)

wherein $R^{1a}$, $R^2$ and L are as defined above, a compound represented by the formula (III-1) or its salt:

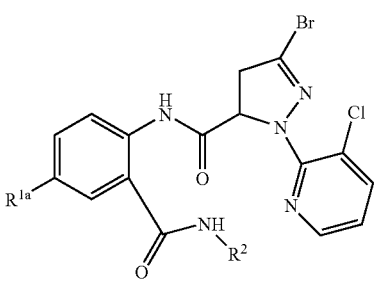

(III-1)

wherein $R^{1a}$ and $R^2$ are as defined above, a compound represented by the formula (X-1) or its salt:

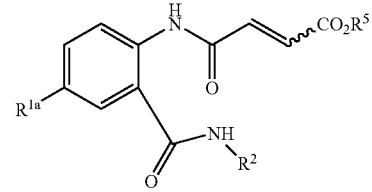

(X-1)

wherein $R^5$ is alkyl, and $R^{1a}$ and $R^2$ are as defined above; and a compound represented by the formula (XI-1) or its salt:

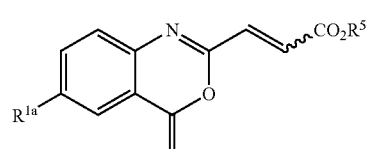

(XI-I)

wherein $R^{1a}$ and $R^5$ are as defined above.

The alkyl or alkyl moiety in $R^{1a}$, $R^2$, $R^3$, $R^4$ or $R^5$ may be linear or branched $C_{1-6}$ alkyl such as methyl, ethyl, propyl, isopropyl, butyl, isobutyl, tert-butyl, pentyl or hexyl. Further, the alkyl moiety in "$C_{5-10}$ alkyloxy" as $R^4$ may be linear or branched.

The halogen or halogen as the substituent in $R^{1a}$ or $R^3$ may be an atom of fluorine, chlorine, bromine or iodine. The number of halogens as substituents may be 1 or more, and if more, the respective halogens may be the same or different. Further, the positions for substitution of such halogens may be any positions.

The substituent of phenoxy, benzyloxy, phenylthio or benzylthio as $R^4$ may be a chlorine atom, a bromine atom, methyl, methoxy or nitro.

The compounds of the formulae (X-1) and (XI-1) have cis- and trans-isomers, and each compound may be any one of such isomers or a mixture thereof.

The salt of the above compound includes all kinds so long as they are agriculturally acceptable. It may, for example, an alkali metal salt such as a sodium salt or a potassium salt; an alkaline earth metal salt such as a magnesium salt or a calcium salt; an ammonium salt such as a dimethylammonium salt or a triethylammonium salt; an inorganic acid salt such as a hydrochloride, a perchlorate, a sulfate or a nitrate; or an organic acid salt such as an acetate or a methanesulfonate.

Effects of the Invention

According to the process of the present invention, an anthranilamide compound having halogen atoms at specific positions in the benzene ring and the pyrazole ring or its salt can be efficiently produced.

BEST MODE FOR CARRYING OUT THE INVENTION

Now, the process for producing an anthranilamide compound or its salt of the present invention will be described in detail below.

The anthranilamide compound of the formula (I) or its salt can be produced in accordance with the following reaction [A] and a conventional process for producing a salt:

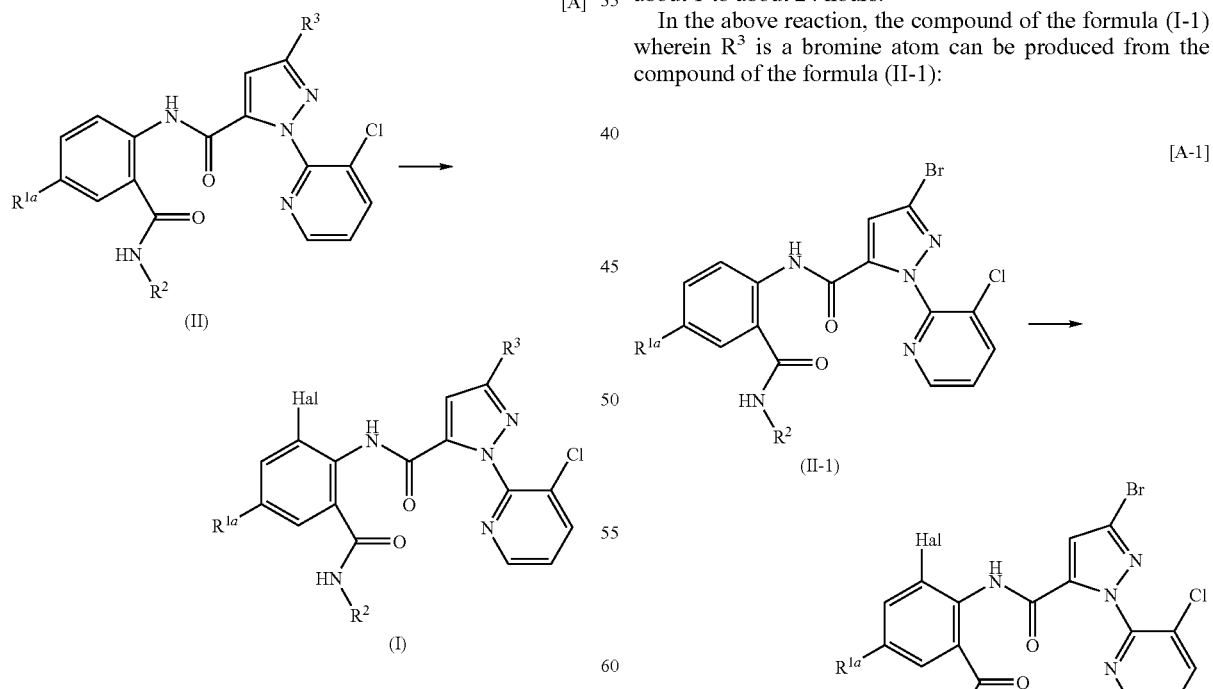

wherein $R^{1a}$, $R^2$, $R^3$ and Hal are as defined above.

The reaction [A] may be carried out by treating the compound of the formula (II) with a halogenating agent usually in the presence of a base and a solvent.

The compound of the formula (II) may, for example, be 3-bromo-N-[4-chloro-2-(1-cyclopropylethylcarbamoyl)phenyl]-1-(3-chloropyridin-2-yl)-1H-pyrazole-5-carboxamide, 3-bromo-N-[4-chloro-2-(cyclopropylmethylcarbamoyl)phenyl]-1-(3-chloropyridin-2-yl)-1H-pyrazole-5-carboxamide or N-[4-chloro-2-(1-cyclopropylethylcarbamoyl)phenyl]-3-trifluoromethyl-1-(3-chloropyridin-2-yl)-1H-pyrazole-5-carboxamide.

As the halogenating agent, chlorine or bromine may be selected.

As the base, one or more types may suitably be selected from, for example, metal hydroxides such as sodium hydroxide, lithium hydroxide, potassium hydroxide and calcium hydroxide, alkali metal hydrides such as sodium hydride and potassium hydride, and alkali metal alkoxides such as sodium methoxide, sodium ethoxide and potassium tert-butoxide. The base can be used in an amount of from 0.8 to 5 times by mol, preferably from 1 to 3.5 times by mol, to the compound of the formula (II).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; ketones such as acetone, methyl ethyl ketone and cyclohexanone; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The reaction [A] can be carried out usually at from −20 to 120° C., preferably at from 0 to 80° C., and the reaction time is usually from about 0.5 to about 48 hours, preferably from about 1 to about 24 hours.

In the above reaction, the compound of the formula (I-1) wherein $R^3$ is a bromine atom can be produced from the compound of the formula (II-1):

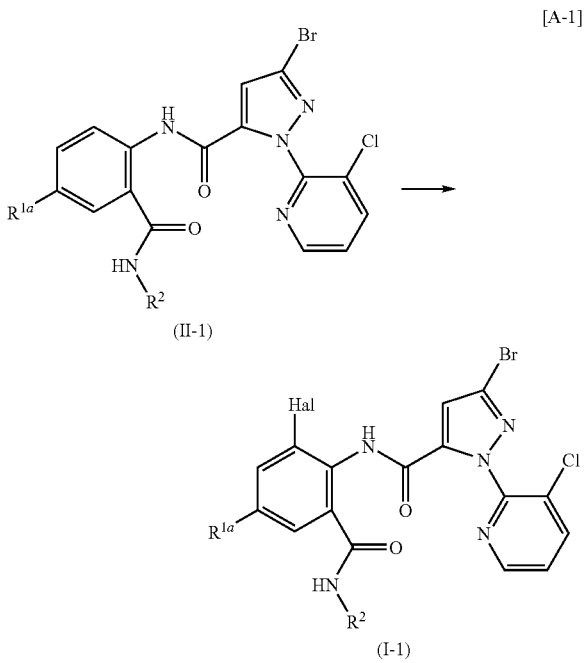

wherein $R^{1a}$, $R^2$ and Hal are as defined above.

A compound of the formula (II-A) including the compound of the formula (II-1) to be used in the reaction [A] can be produced by processes [B] to [M] or [N] to [Q].

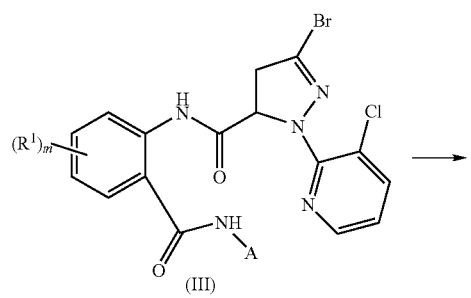

[B]

wherein $R^1$ is alkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, nitro, formyl or cyano, A is alkyl substituted by Y; Y is $C_{3-4}$ cycloalkyl which may be substituted by at least one substituent selected from the group consisting of halogen, alkyl and haloalkyl, and m is 0 to 4.

The alkyl or alkyl moiety in $R^1$, A or Y may be linear or branched. As its specific example, $C_{1-6}$ alkyl such as methyl, ethyl, propyl, isopropyl, butyl, tert-butyl, pentyl or hexyl may be mentioned.

The alkenyl or alkenyl moiety in $R^1$ may be linear or branched. As its specific example, $C_{2-6}$ alkenyl such as vinyl, 1-propenyl, allyl, isopropenyl, 1-butenyl, 1,3-butadienyl or 1-hexenyl may be mentioned.

The alkynyl or alkynyl moiety in $R^1$ may be linear or branched. As its specific example, $C_{2-6}$ alkynyl such as ethynyl, 2-butynyl, 2-pentynyl or 3-hexynyl may be mentioned.

As the halogen or halogen as the substituent in $R^1$ or Y, an atom of fluorine, chlorine, bromine or iodine may be mentioned. The number of halogens as substituents may be 1 or more, and if more, the respective halogens may be the same or different. Further, the positions for substitution of such halogens may be any positions.

The reaction [B] can be carried out usually by treating a compound of the formula (III) with an oxidizing agent in the presence of a solvent to produce an anthranilamide compound represented by the formula (II-A).

The compound of the formula (III) may, for example, be 3-bromo-N-(4-chloro-2-(1-cyclopropylethylcarbamoyl)phenyl)-1-(3-chloropyridin-2-yl)-4,5-dihydro-1H-pyrazole-5-carboxamide, 3-bromo-N-(2-bromo-4-chloro-6-(1-cyclopropylethylcarbamoyl)phenyl)-1-(3-chloropyridin-2-yl)-4,5-dihydro-1H-pyrazole-5-carboxamide, 3-bromo-N-(4-chloro-2-(1-cyclopropylethylcarbamoyl)-6-methylphenyl)-1-(3-chloropyridin-2-yl)-4,5-dihydro-1H-pyrazole-5-carboxamide, 3-bromo-N-(2-bromo-4-chloro-6-(cyclopropylmethylcarbamoyl)phenyl)-1-(3-chloropyridin-2-yl)-4,5-dihydro-1H-pyrazole-5-carboxamide or 3-bromo-N-(4-chloro-2-(cyclopropylmethylcarbamoyl)phenyl)-1-(3-chloropyridin-2-yl)-4,5-dihydro-1H-pyrazole-5-carboxamide.

The oxidizing agent may, for example, be 2,3-dichloro-5,6-dicyano-1,4-benzoquinone, chloranil, o-chloranil, hydrogen peroxide, ammonium peroxydisulfate, sodium peroxydisulfate, potassium peroxydisulfate, potassium permanganate, OXONE (tradename), sodium hypochlorite, sodium chlorite, benzoyl peroxide, tert-butyl hydroperoxide or oxygen. The oxidizing agent can be used in an amount of from 1 to 10 times by mol, preferably from 1 to 4.5 times by mol, to the compound of the formula (III).

The solvent may be any solvent so long as it is inert to the reaction. For example, one or more types may suitably be selected from, for example, ethers such as tetrahydrofuran, dioxane and dimethoxyethane; ketones such as acetone and methyl ethyl ketone; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; acetic acid and water.

The reaction [B] can be carried out usually at from 0 to 150° C., preferably at from 15 to 120° C., and the reaction time is usually from about 0.5 to about 50 hours.

In the above reaction, the compound of the formula (II-1) can be produced from a compound of the formula (III-1):

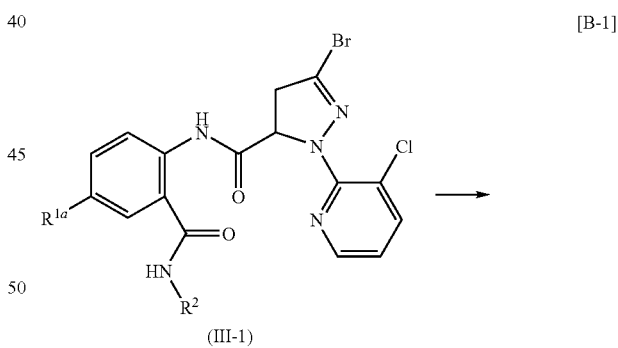

[B-1]

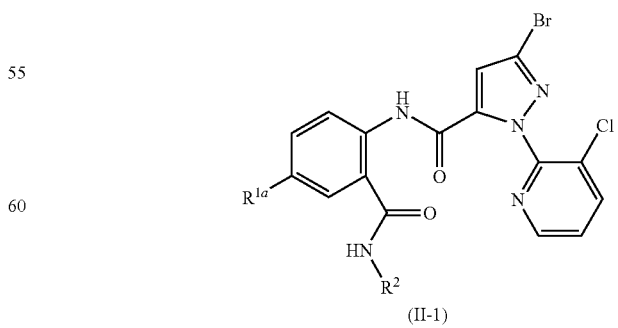

wherein $R^{1a}$ and $R^2$ are as defined above.

The compound of the above formula (III) can be produced in accordance with the reaction [C]:

[C]

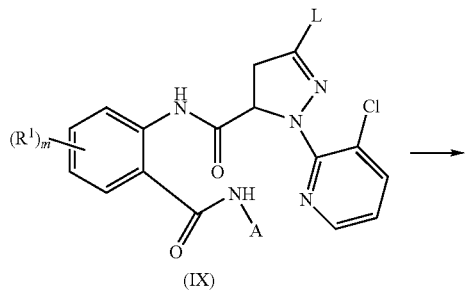

(IX)

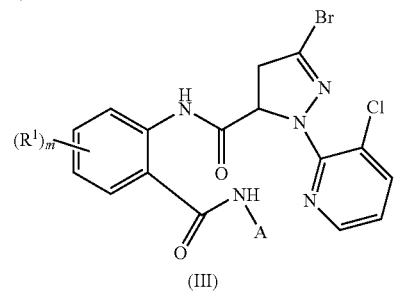

(III)

wherein $R^1$, A, L and m are as defined above.

The reaction [C] can be carried out usually by treating the compound of the formula (IX) with a brominating agent in an equimolar amount or more in the presence of a solvent.

The compound of the formula (IX) may, for example, be 5-(4-chloro-2-(1-cyclopropylethylcarbomoyl)phenylcarbamoyl)-1-(3-chloropyridin-2-yl)-4,5-dihydro-1H-pyrazol-3-yl 4-methylbenzene sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl 4-methylbenzene sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl 4-methylbenzene sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl 4-methylbenzene sulfonate, 5-(4-chloro-2-(1-cyclopropylethylcarbamoyl)phenylcarbamoyl)-1-(3-chloropyridin-2-yl)-4,5-dihydro-1H-pyrazol-3-yl methanesulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl methanesulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl methanesulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl methanesulfonate or 5-(4-chloro-2-(cyclopropylmethylcarbamoyl)phenylcarbamoyl)-1-(3-chloropyridin-2-yl)-4,5-dihydro-1H-pyrazol-3-yl methanesulfonate.

As the brominating agent, one or more types may suitably be selected from, for example, bromine and metal bromides such as sodium bromide, potassium bromide, lithium bromide, ammonium bromide, magnesium bromide, calcium bromide, barium bromide, aluminum bromide, phosphorus tribromide, phosphorus pentabromide, iron bromide, copper bromide and zinc bromide.

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; polar aprotic solvents such as acetone, methyl ethyl ketone, cyclohexanone, acetonitrile, propionitrile, N,N-dimethylformamide, dimethyl sulfoxide, hexamethylphosphoric triamide, sulfolane, dimethylacetamide and N-methylpyrrolidone; and protic solvents such as acetic acid.

The reaction [C] can be carried out usually at from −10 to 150° C., preferably at from 0 to 120° C., and the reaction time is usually from about 0.1 to about 24 hours.

In the above reaction, the compound of the formula (III-1) can be produced from a compound of the formula (IX-1):

[C-1]

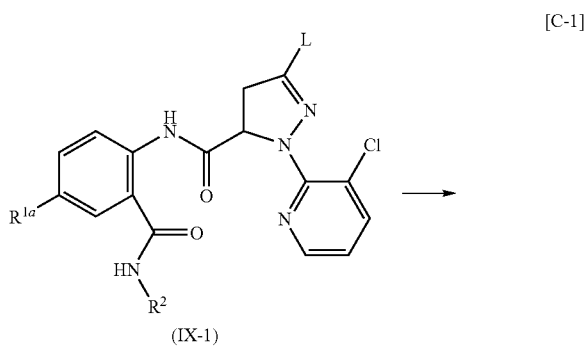

(IX-1)

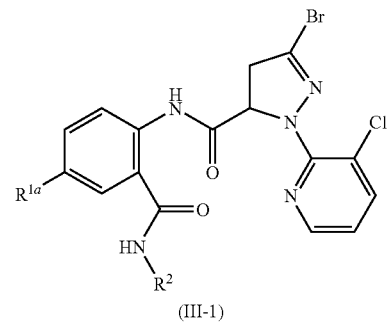

(III-1)

wherein $R^{1a}$, $R^2$ and L are as defined above.

The compound of the above formula (IX) can be produced in accordance with the reaction [D]:

[D]

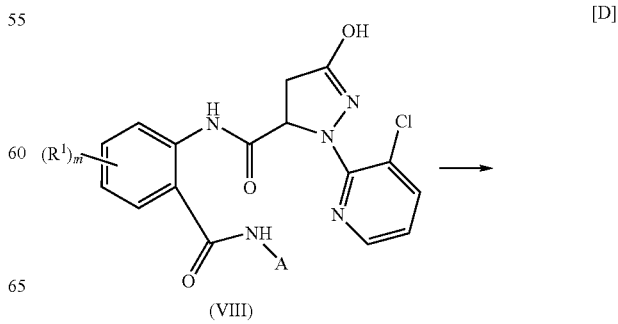

(VIII)

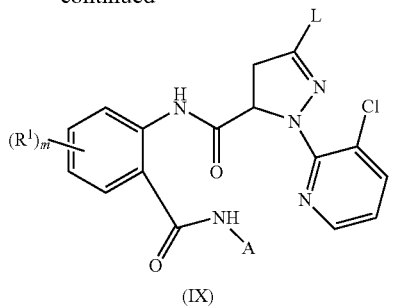

(IX)

wherein R¹, A, L and m are as defined above.

The reaction [D] can be carried out usually by treating the compound of the formula (VIII) with a sulfonyl chloride, a chlorinating agent or an acid chloride in an equimolar amount or more in the presence of a base and a solvent.

The compound of the formula (VIII) may, for example, be N-(4-chloro-2-(1-cyclopropylethylcarbamoyl)phenyl)-1-(3-chloropyridin-2-yl)-3-hydroxy-4,5-dihydro-1H-pyrazol-5-carboxamide, N-(2-bromo-4-chloro-6-(1-cyclopropylethylcarbamoyl)phenyl)-1-(3-chloropyridin-2-yl)-3-hydroxy-4,5-dihydro-1H-pyrazole-5-carboxamide, N-(4-chloro-2-(1-cyclopropylethylcarbamoyl)-6-methylphenyl)-1-(3-chloropyridin-2-yl)-3-hydroxy-4,5-dihydro-1H-pyrazole-5-carboxamide, N-(2-bromo-4-chloro-6-(cyclopropylmethylcarbamoyl)phenyl)-1-(3-chloropyridin-2-yl)-3-hydroxy-4,5-dihydro-1H-pyrazole-5-carboxamide or N-(4-chloro-2-(cyclopropylmethylcarbamoyl)phenyl)-1-(3-chloropyridin-2-yl)-3-hydroxy-4,5-dihydro-1H-pyrazole-5-carboxamide.

The sulfonyl chloride may, for example, be p-toluenesulfonyl chloride or methanesulfonyl chloride. The chlorinating agent may, for example, be p-toluenesulfonyl chloride, methanesulfonyl chloride, thionyl chloride, oxalyl dichloride, phosphorus trichloride or phosphorus pentachloride. The acid chloride may, for example, be acetyl chloride, methyl chlorocarbonate or ethyl chlorocarbonate.

As the base, one or more types may suitably be selected from, for example, inorganic bases such as sodium hydroxide, lithium hydroxide, potassium hydroxide, calcium hydroxide, sodium carbonate and potassium carbonate; alkali metal alkoxides such as sodium t-butoxide and potassium t-butoxide; alkali metal hydrides such as sodium hydride and potassium hydride; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 1 to 5 times by mol, preferably from 1 to 3 times by mol, to the compound of the formula (VIII).

The solvent may be any solvent so long as it is inert to the reaction. For example, one or more types may suitable be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; and polar aprotic solvents such as acetonitrile, propionitrile, N,N-dimethylformamide and dimethyl sulfoxide.

The reaction [D] can be carried out usually at from −20 to 140° C., preferably at from −10 to 120° C., and the reaction time is usually from about 0.1 to about 10 hours.

In the above reaction, the compound of the formula (IX-1) can be produced from a compound of the formula (VIII-1):

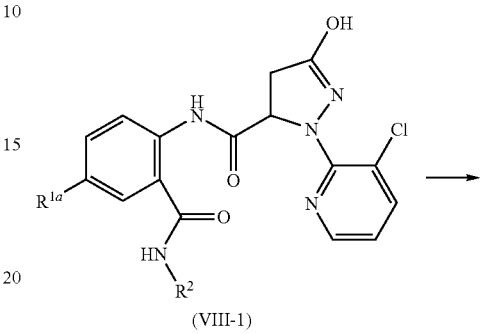

(VIII-1)

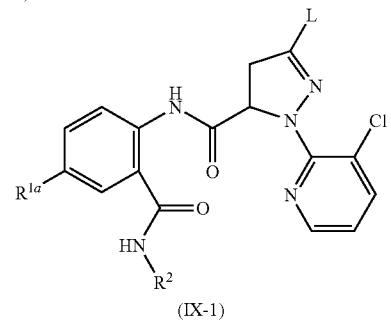

(IX-1)

wherein $R^{1a}$, $R^2$ and L are as defined above.

The compound of the above formula (VIII) can be produced in accordance with the reaction [E]:

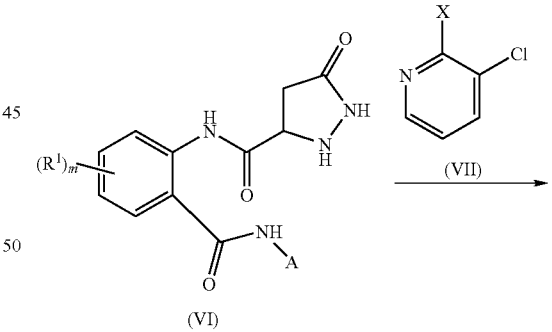

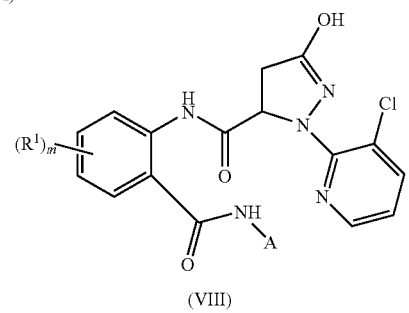

(VIII)

wherein R¹, A, X and m are as defined above.

The reaction [E] can be carried out usually by treating the compound of the formula (VI) with the compound of the formula (VII) in the presence of a base and a solvent in an inert gas atmosphere.

The compound of the formula (VI) may, for example, be N-(4-chloro-2-(1-cyclopropylethylcarbamoyl)phenyl)-5-oxopyrazolidine-3-carboxamide, N-(2-bromo-4-chloro-6-(1-cyclopropylethylcarbamoyl)phenyl)-5-oxopyrazolidine-3-carboxamide, N-(4-chloro-2-(1-cyclopropylethylcarbamoyl)-6-methylphenyl)-5-oxopyrazolidine-3-carboxamide, N-(2-bromo-4-chloro-6-(cyclopropylmethylcarbamoyl)phenyl)-5-oxopyrazolidine-3-carboxamide or N-(4-cholo-2-(cyclopropylmethylcarbamoyl)phenyl)-5-oxopyrazolidine-3-carboxamide.

The inert gas may be gas of e.g. nitrogen or argon.

As the base, one or more types may suitably be selected from, for example, inorganic bases such as sodium hydroxide, lithium hydroxide, potassium hydroxide, calcium hydroxide, sodium carbonate, potassium carbonate, cesium carbonate, sodium hydride, potassium hydride and tripotassium phosphate hydrate; and organic bases such as sodium t-butoxide, potassium t-butoxide, sodium ethoxide, sodium methoxide, trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base may be used in an amount of from 1 to 5 times by mol, preferably from 1 to 3.5 times by mol, to the compound of the formula (VI).

The solvent may be any solvent so long as it is inert to the reaction. For example, one or more types may suitably be selected from, for example, alcohols such as methanol, ethanol, propanol, butanol, isopropyl alcohol and 2-methyl-2-propanol; ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

A metal catalyst may be added so as to accelerate the present reaction. As the metal catalyst, one or more types may suitably be selected from palladium catalysts such as palladium-carbon, palladium chloride, palladium acetate, tetrakis (triphenylphosphine)palladium and bis(triphenylphosphine) palladium dichloride. The metal catalyst can be used in an amount of from 0.005 to 2.5 times by mol, preferably from 0.01 to 1 time by mol, to the compound of the formula (VI).

The reaction [E] can be carried out usually at from 0 to 150° C., preferably at from 25 to 120° C., and the reaction time is usually from about 0.5 to about 50 hours.

In the above reaction, the compound of the formula (VIII-1) can be produced from a compound of the formula (VI-1):

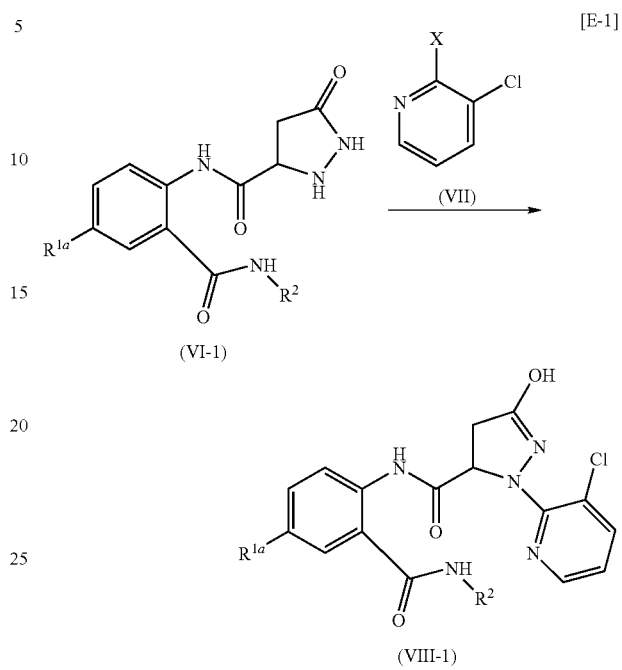

wherein $R^{1a}$, $R^2$ and X are as defined above.

The compound of the above formula (VI) can be produced usually by treating a compound of the formula (X) with hydrazine in the presence of a solvent:

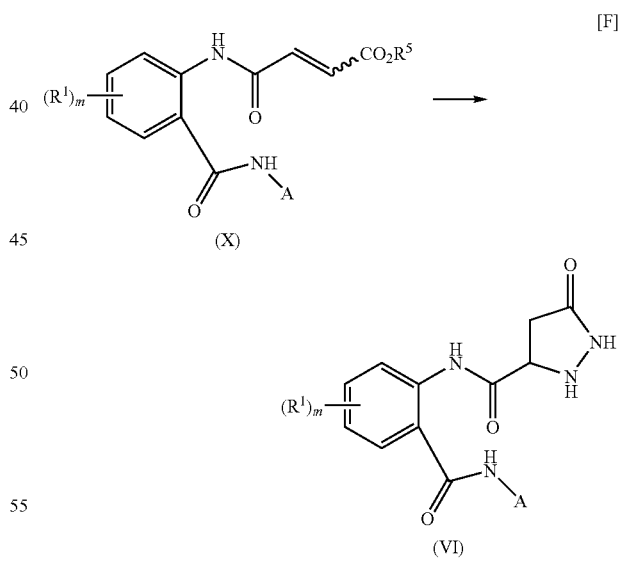

wherein $R^1$, $R^5$, A and m are as defined above.

The compound of the formula (X) has cis- and trans-isomers, and it may be any one of such isomers or a mixture thereof.

The compound of the formula (X) may, for example, be methyl 4-(4-chloro-2-(1-cyclopropylethylcarbamoyl)phenylamino)-4-oxocrotonate, methyl 4-(2-bromo-4-chloro-6-(1-cyclopropylethylcarbamoyl)phenylamino)-4-oxocrotonate, ethyl 4-(2-bromo-4-chloro-6-(1-cyclopropylethylcarbamoyl)phenylamino)-4-oxocrotonate, methyl 4-(4-chloro-2-(1- cyclopropylethylcarbamoyl)-6-methylphenylamino)-4-oxo-crotonate, methyl 4-(2-bromo-4-chloro-6-(cyclopropylmethylcarbamoyl)phenylamino)-4-oxocrotonate, methyl 4-(4-chloro-2-(1-cyclopropylethylcarbamoyl)phenylamino)-4-oxoisocrotonate, methyl 4-(2-bromo-4-chloro-6-(1-cyclopropylethylcarbamoyl)phenylamino)-4-oxoisocrotonate, ethyl 4-(2-bromo-4-chloro-6-(1-cyclopropylethylcarbamoyl)phenylamino)-4-oxoisocrotonate, methyl 4-(4-chloro-2-(1-cyclopropylethylcarbamoyl)-6-methylphenylamino)-4-oxoisocrotonate, methyl 4-(2-bromo-4-chloro-6-(cyclopropylmethylcarbamoyl)phenylamino)-4-oxoisocrotonate, ethyl 4-(4-chloro-2-(1-cyclopropylethylcarbamoyl)phenylamino)-4-oxocrotonate, ethyl 4-(4-chloro-2-(cyclopropylmethylcarbamoyl)phenylamino)-4-oxocrotonate or methyl 4-(4-chloro-2-(1-cyclopropylethylcarbamoyl)phenylamino)-4-oxoisocrotonate.

Hydrazine can be used in an amount of from 0.9 to 1.5 times by mol, preferably from 1 to 1.2 times by mol, to the compound of the formula (X).

The solvent may be any solvent so long as it is inert to the reaction. For example, one or more types may suitably be selected from, for example, protic solvents such as methanol, ethanol, propanol, butanol, isopropyl alcohol, 2-methyl-2-propanol and water; ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as N,N-dimethylformamide, dimethyl sulfoxide, hexamethylphosphoric triamide, sulfolane, N,N-dimethylacetamide and N-methylpyrrolidone.

The present reaction can be carried out usually at from −10 to 150° C., preferably at from 0 to 120° C., and the reaction time is usually from about 0.2 to about 20 hours.

In the above reaction, the compound of the formula (VI-1) can be produced from a compound of the formula (X-1):

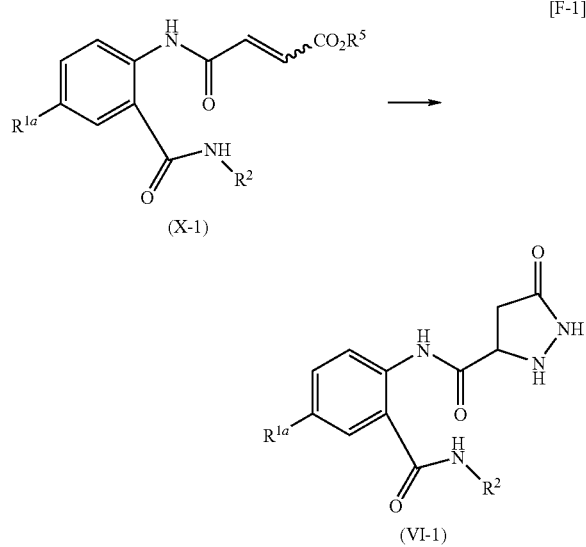

wherein $R^{1a}$, $R^2$ and $R^5$ are as defined above.

The compound of the formula (X) can be produced in accordance with [G]:

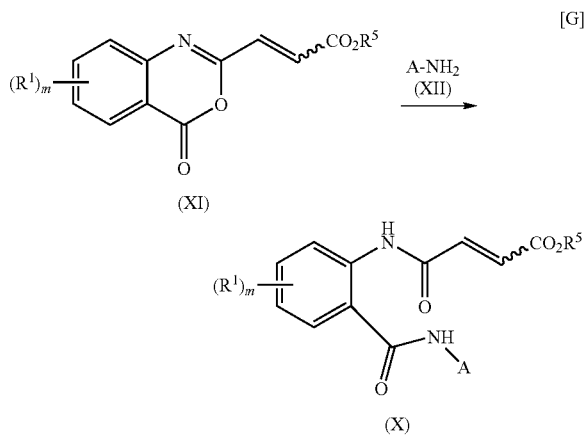

wherein $R^1$, $R^5$, A and m are as defined above.

The compounds (X) and (XI) have cis- and trans-isomers, and each compound may be any one of such isomers or a mixture thereof.

The reaction [G] can be carried out usually by treating the compound of the formula (XI) with the compound of the formula (XII) in the presence of a solvent or by treating the compound of the formula (XI) with a salt of the compound of the formula (XII) in the presence of a solvent and a base.

The compound of the formula (XI) may, for example, be methyl (E)-3-(6-chloro-4-oxo-4H-benzo[d][1,3]oxazin-2-yl)acrylate, methyl (E)-3-(8-bromo-6-chloro-4-oxo-4H-benzo[d][1,3]oxazin-2-yl)acrylate, ethyl (E)-3-(8-bromo-6-chloro-4-oxo-4H-benzo[d][1,3]oxazin-2-yl)acrylate, methyl (E)-3-(6-chloro-8-methyl-4-oxo-4H-benzo[d][1,3]oxazin-2-yl)acrylate, methyl (Z)-3-(6-chloro-4-oxo-4H-benzo[d][1,3]oxazin-2-yl)acrylate, methyl (Z)-3-(8-bromo-6-chloro-4-oxo-4H-benzo[d][1,3]oxazin-2-yl)acrylate, ethyl (Z)-3-(8-bromo-6-chloro-4-oxo-4H-benzo[d][1,3]oxazin-2-yl) acrylate, methyl (Z)-3-(6-chloro-8-methyl-4-oxo-4H-benzo[d][1,3]oxazin-2-yl)acrylate or ethyl (E)-3-(6-chloro-4-oxo-4H-benzo[d][1,3]oxazin-2-yl)acrylate.

Further, as the compound of the formula (XII), α-methyl-cyclopropylmethylamine, α-methyl-cyclobutylmethylamine, cyclopropylmethylamine or the like may be used. As the salt of the compound of the formula (XII), a salt of an inorganic acid such as hydrochloride or sulfate; a salt of an organic acid such as acetate or methanesulfonate or the like may be used. The compound of the formula (XII) or its salt can be used in an equimolar amount or more, preferably from 1 to 5 times by mol to the compound of the formula (XI).

In a case where a salt of the compound of the formula (XII) is used, a base is preferably used. As the base, for example, one or more types may suitably be selected from, for example, inorganic bases such as sodium hydroxide, potassium hydroxide, sodium hydride, potassium hydride, sodium carbonate, potassium carbonate, sodium hydrogen carbonate and potassium hydrogen carbonate; alkali metal alkoxides such as sodium t-butoxide and potassium t-butoxide; and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 1.5 times by mol, to the salt of the compound of the formula (XII).

The solvent may be any solvent so long as it is inert to the reaction. For example, one or more types may suitably be selected from, for example, ethers such as diethyl ether, tetrahydrofuran, dioxane and dimethoxyethane; halogenated hydrocarbons such as methylene chloride, chloroform, carbon tetrachloride and chlorobenzene; aromatic hydrocarbons such as benzene, toluene and xylene; and polar aprotic solvents such as acetonitrile, N,N-dimethylformamide, dimethylacetamide, N-methylpyrrolidone and dimethyl sulfoxide.

The present reaction can be carried out usually at from −20 to 120° C., preferably at from 0 to 80° C., and the reaction time is usually from about 0.5 to about 24 hours.

In the above reaction, the compound of the formula (X-1) can be produced from a compound of the formula (XI-1):

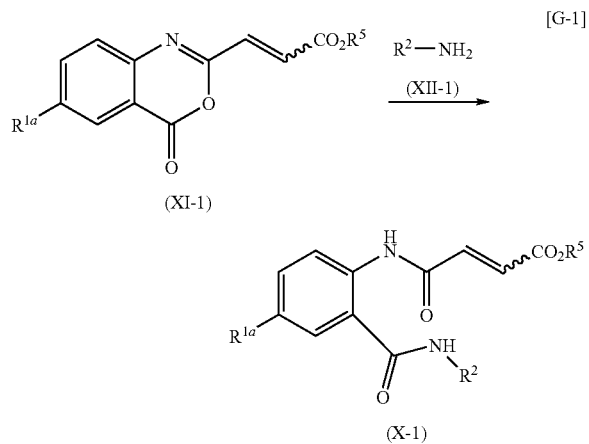

wherein $R^{1a}$, $R^2$ and $R^5$ are as defined above.

The compound of the above formula (X) can be produced also by a process of the reaction [H] or [I]:

(H)

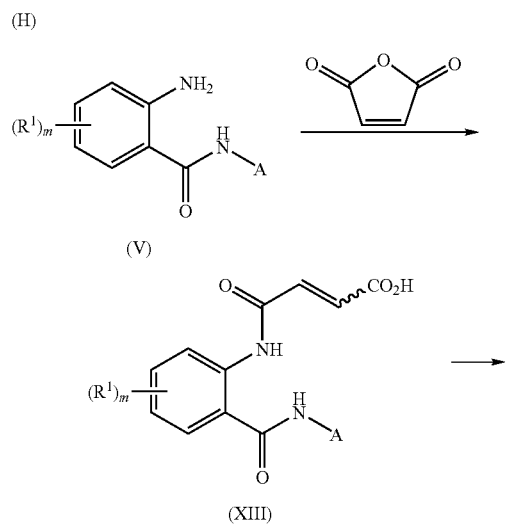

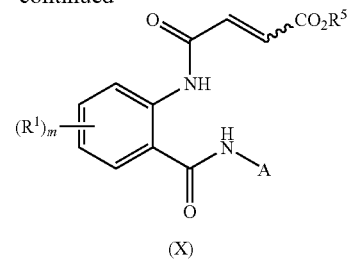

wherein $R^1$, $R^5$, A and m are as defined above. The compounds (X) and (XIII) have cis- and trans-isomers, and each compound may be any one of such isomers or a mixture thereof.

The compound of the formula (V) which can be used in the above reaction may, for example, be 2-amino-5-chloro-N-(1-cyclopropylethyl)benzamide, 2-amino-3-bromo-5-chloro-N-(1-cyclopropylethyl)benzamide, 2-amino-5-chloro-3-methyl-N-(1-cyclopropylethyl)benzamide or 2-amino-3-bromo-5-chloro-N-(cyclopropylmethyl)benzamide.

The first step reaction of the reaction [H] can be carried out usually by treating the compound of the formula (V) with maleic anhydride in the presence of a solvent.

Maleic anhydride can be used in an amount of from 0.9 to 3 times by mol, preferably from 1 to 1.5 times by mol to the compound of the formula (V).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; and polar aprotic solvents such as acetone, methyl ethyl ketone, acetonitrile, propionitrile, N,N-dimethylformamide, dimethyl sulfoxide, hexamethylphosphoric triamide, sulfolane, dimethylacetamide and N-methylpyrrolidone, and acetic acid.

The present reaction may be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; and organic bases such as alkali metal alkoxides such as sodium t-butoxide and potassium t-butoxide, trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the compound of the formula (V).

The present reaction can be carried out usually at from 0 to 150° C., preferably at from 20 to 110° C., and the reaction time is usually from about 0.5 to about 24 hours.

The second step reaction of the reaction [H] can be carried out usually by treating the compound of the formula (XIII) with an alcohol represented by $R^5$—OH in an equimolar amount or more in the presence of an acid.

The alcohol may suitably be selected from methanol, ethanol, propanol, butanol, isopropyl alcohol and the like.

As the acid, one or more types may suitably be selected from, for example, hydrogen halides such as hydrogen chloride, hydrogen bromide and hydrogen iodide; inorganic acids such as sulfuric acid, sulfurous acid, nitric acid, nitrous acid, phosphoric acid, boric acid, chloric acid, chlorous acid and hypochlorous acid; Lewis acids such as titanium halide, aluminum halide, iron halide, tin halide, zinc halide, magnesium halide, silicon halide, copper halide and trifluoroborane-ether complex; and organic acids such as formic acid, $C_{1-6}$ alkyl carboxylic acid, aromatic carboxylic acid, $C_{1-6}$ alkyl sulfonic acid and aromatic sulfonic acid. The acid can be used in an amount of from 0.05 to 10 times by mol, preferably from 0.1 to 5 times by mol to the compound (XIII).

The present reaction may be carried out in the presence of a solvent if desired. The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, N,N-dimethylacetamide and N-methylpyrrolidone.

The present reaction can be carried out usually at from 0 to 100° C., preferably at from 10 to 50° C., and the reaction time is usually from about 1 to about 50 hours.

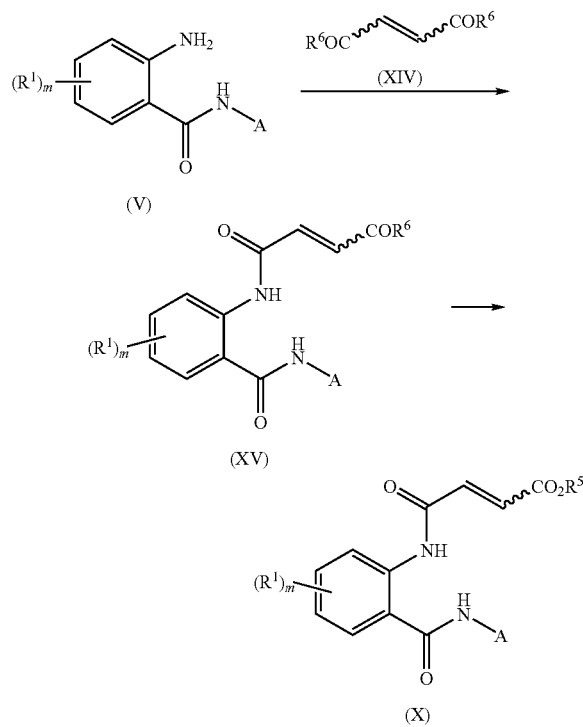

wherein $R^6$ is a chlorine atom or a bromine atom, and $R^1$, $R^5$, A and m are as defined above. The compounds of the formulae (X), (XIV) and (XV) have cis- and trans-isomers, and each compound may be any one of such isomers or a mixture thereof.

The first step reaction in the reaction [I] can be carried out usually by treating the compound of the formula (V) with the compound of the formula (XIV) in the presence of a solvent. The compound of the formula (XIV) can be used in an amount of from 0.9 to 3 times by mol, preferably from 1 to 1.5 times by mol to the compound of the formula (V).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The present reaction may be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; alkali metal alkoxides such as sodium t-butoxide and potassium t-butoxide, and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the compound of the formula (V).

The present reaction can be carried out usually at from −10 to 150° C., preferably at from 0 to 50° C., and the reaction time is usually from about 0.5 to about 24 hours.

The second step reaction of the reaction [I] can be carried out usually by treating the compound of the formula (XV) with an alcohol represented by $R^5$—OH in an equimolar amount or more in the presence of a solvent.

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The present reaction may be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; alkali metal alkoxides such as sodium t-butoxide and potassium t-butoxide, organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N- dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the alcohol.

The present reaction can be carried out usually at from −10 to 150° C., preferably at from 0 to 50° C., and the reaction time is usually from about 0.5 to about 24 hours.

Further, the compound of the formula (XI) to be used in the above reaction [G] can be produced in accordance with the reaction [J] or [K]:

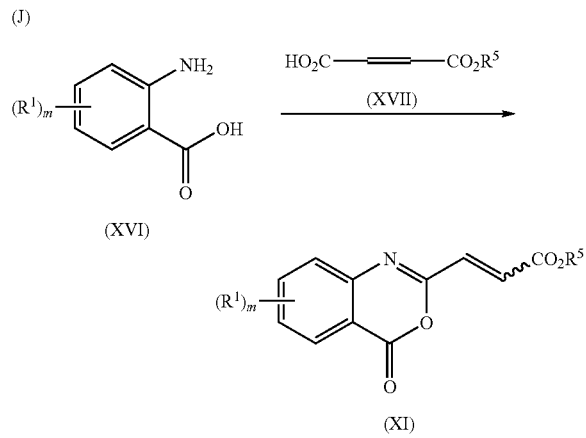

wherein $R^1$, $R^5$ and m are as defined above. The compounds of the formulae (XVI) and (XVII) have cis- and trans-isomers, and each compound may be any one of such isomers or a mixture thereof.

The reaction [J] can be carried out usually by reacting the compound of the formula (XVII) with an acid chloride in the presence of a base and a solvent to convert it to an active derivative, which is reacted with the compound of the formula (XVI) in the presence of a base, followed by addition of an activator for reaction.

The compound of the formula (XVI) which can be used in the above reaction may, for example, be 5-chloroanthranilic acid, 3-bromo-5-chloroanthranilic acid or 5-chloro-3-methylanthranilic acid, and as the compound of the formula (XVII), maleic acid monomethyl ester, maleic acid monoethyl ester, maleic acid monopropyl ester or the like may be used.

The above reaction can be carried out in the presence of a solvent, and a series of the reactions can be carried out in the same solvent. The solvent may be any solvent so long as it is inert to the reaction. For example, one or more types may suitably be selected from, for example, halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; ethers such as diethyl ether, butyl methyl ether, tetrahydrofuran, dioxane and dimethoxyethane; esters such as methyl acetate, ethyl acetate and propyl acetate; ketones such as acetone, 2-butanone and 4-methyl-2-pentanone; and polar aprotic solvents such as acetonitrile, propionitrile and N,N-dimethylformamide.

As the acid chloride, a chlorocarbonate, sulfonyl chloride, carbonyl chloride or the like may be used. The chlorocarbonate may, for example, be methyl chlorocarbonate, ethyl chlorocarbonate or isopropyl chlorocarbonate, the sulfonyl chloride may, for example, be methanesulfonyl chloride, propanesulfonyl chloride, benzenesulfonyl chloride or p-toluenesulfonyl chloride, and the carbonyl chloride may, for example, be acetyl chloride or propionyl chloride, and methanesulfonyl chloride is preferred. This reagent is used in an amount of from 1.0 to 3.0 times by mol, preferably from 1.1 to 2.0 times by mol to the compound of the formula (XVII).

The base may, for example, be pyridine, 2-picoline, 3-picoline, 2,6-lutidine, triethylamine or 4-dimethylaminopyridine. The base is used in an amount of from 1.0 to 2.0 times by mol, preferably from 1.2 to 1.7 times by mol to the compound of the formula (XVI).

The reaction can be carried out usually at from −30 to 60° C., preferably at from −10 to 40° C., and the reaction time is usually from about 5 minutes to about 1 hour.

After the compound of the formula (XVII) is converted to an active derivative, the amount of the compound of the formula (XVI) to be reacted is from 0.9 to 1.2 times by mol, preferably from 1.0 to 1.05 times by mol to the compound of the above formula (XVII).

As the base, one used in the above conversion to the active derivative can be used, and its amount is from 2 to 4 times by mol, preferably from 2.9 to 3.5 times by mol to the compound of the above formula (XVI). The compound of the formula (XVI) and the base may be added in the form of a mixed solution with the solvent.

The reaction can be carried out usually at from −30 to 60° C., preferably at from −10 to 40° C. and the reaction time is usually from about 5 minutes to about 1 hour.

As the activating agent, a chlorocarbonate, sulfonyl chloride or the like may be used. The chlorocarbonate may, for example, be methyl chlorocarbonate, ethyl chlorocarbonate or isopropyl chlorocarbonate, and the sulfonyl chloride may, for example, be methanesulfonyl chloride, propanesulfonyl chloride, benzenesulfonyl chloride or p-toluenesulfonyl chloride, and methanesulfonyl chloride is preferred. The activating agent is used in an amount of from 1.0 to 1.5 times by mol, preferably from 1.1 to 1.3 times by mol to the compound of the formula (XVI). The activating agent is preferably the same as the above described acid chloride, and it may be added in the form of a mixture with the solvent.

The reaction can be carried out usually at from −30 to 60° C., preferably at from −10 to 40° C., and the reaction time is usually from about 1 to about 24 hours.

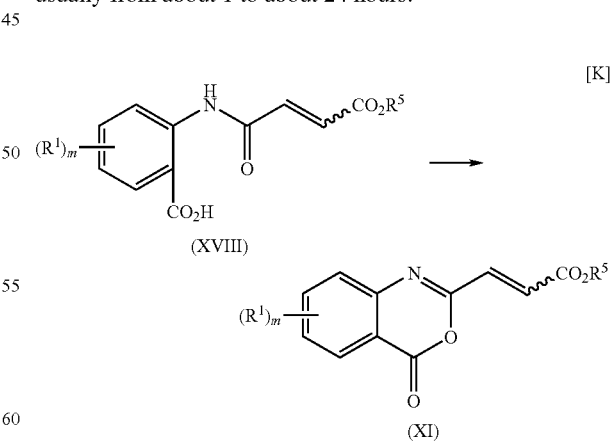

wherein $R^1$, $R^5$ and m are as defined above.

The compound of the formula (XI) can be produced also by converting the compound of the formula (XVIII) to an active derivative in the presence of a solvent, followed by cyclization.

As the reagent for conversion to the active derivative, a chlorocarbonate, sulfonyl chloride, thionyl chloride, carbonyl chloride, carboxylic anhydride, phosphorus chloride or the like may be used. The chlorocarbonate may, for example, be methyl chlorocarbonate, ethyl chlorocarbonate or isopropyl chlorocarbonate, the sulfonyl chloride may, for example, be methanesulfonyl chloride, propanesulfonyl chloride, benzenesulfonyl chloride or p-toluenesulfonyl chloride, and the carboxylic anhydride may, for example, be acetic anhydride or propionic anhydride, and methanesulfonyl chloride or acetic anhydride is preferred.

The active reagent is used in an amount of from 1.0 to 1.5 times by mol, preferably from 1.1. to 1.3 times by mol to the compound of the above formula (XVIII), but in a case where the carboxylic anhydride is used as the solvent, it may be used in an amount of from 3 to 20 times by weight to the compound of the above formula (XVIII). The activating agent may be added in the form of a mixture with the solvent. Further, an acid such as sulfuric acid or hydrochloric acid may be added to carry out the reaction.

The solvent may be any solvent so long as it is inert to the reaction. For example, one or more types may suitably be selected from, for example, halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; ethers such as diethyl ether, butyl methyl ether, tetrahydrofuran, dioxane and dimethoxyethane; esters such as methyl acetate, ethyl acetate and propyl acetate; ketones such as acetone, 2-butanone and 4-methyl-2-pentanone; polar aprotic solvents such as acetonitrile, propionitrile and N,N-dimethylformamide; and carboxylic anhydrides such as acetic anhydride and propionic anhydride.

The reaction can be carried out usually at from −30 to 100° C., preferably at from −10 to 60° C., and the reaction time is usually from about 1 to about 24 hours.

The cis-isomer of the compound of the formula (XI) may be isomerized to the trans-isomer by treatment with an acid such as hydrochloric acid.

The compound of the above formula (XVIII) can be produced in accordance with the process [L] or [M]:

(L)

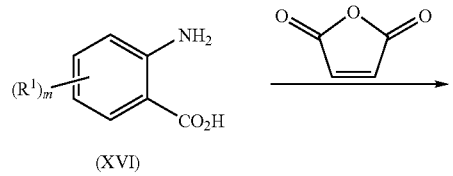

(XVI)

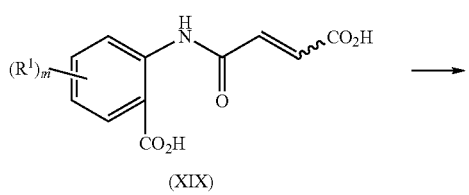

(XIX)

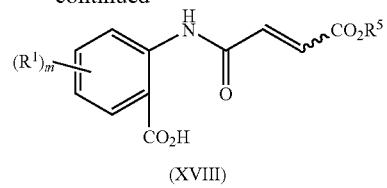

(XVIII)

wherein $R^1$, $R^5$ and m are as defined above. The compounds (XVIII) and (XIX) have cis- and trans-isomers, and each compound may be any one of such isomers or a mixture thereof.

The first step reaction of the reaction [L] can be carried out usually by treating the compound of the formula (XVI) with maleic anhydride in the presence of a solvent. Maleic anhydride can be used in an amount of from 0.9 to 3 times by mol, preferably from 1 to 1.5 times by mol to the compound of the formula (XVI).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; polar aprotic solvents such as acetone, methyl ethyl ketone, acetonitrile, propionitrile, N,N-dimethylformamide, dimethyl sulfoxide, hexamethylphosphoric triamide, sulfolane, dimethylacetamide and N-methylpyrrolidone; and acetic acid.

The present reaction can be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; alkali metal alkoxides such as sodium t-butoxide and potassium t-butoxide, and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the compound of the formula (XVI).

The present reaction can be carried out usually at from 0 to 150° C., preferably at from 20 to 110° C., and the reaction time is usually from about 0.5 to about 24 hours.

The second step reaction of the reaction [L] can be carried out usually by treating the compound of the formula (XIX) with an alcohol represented by $R^5$—OH in an equimolar amount or more in the presence of an acid.

The alcohol may suitably be selected from methanol, ethanol, propanol, butanol, isopropyl alcohol and the like.

As the acid, one or more types may suitably be selected from, for example, hydrogen halides such as hydrogen chloride, hydrogen bromide and hydrogen iodide; inorganic acids such as sulfuric acid, sulfurous acid, nitric acid, nitrous acid, phosphoric acid, boric acid, chloric acid, chlorous acid and hypochlorous acid; Lewis acids such as titanium halide, aluminum halide, iron halide, tin halide, zinc halide, magnesium halide, silicon halide, copper halide and trifluoroborane-ether complex; and organic acids such as formic acid, $C_{1-6}$ alkyl carboxylic acid, aromatic carboxylic acid, $C_{1-6}$ alkyl sulfonic acid and aromatic sulfonic acid. The acid can be used in an amount of from 0.05 to 10 times by mol, preferably from 0.1 to 5 times by mol to the compound (XIX).

The present reaction may be carried out in the presence of a solvent if desired. The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, N,N-dimethylacetamide and N-methylpyrrolidone.

The present reaction can be carried out usually at from 0 to 100° C., preferably at from 10 to 50° C., and the reaction time is usually from about 1 to about 50 hours:

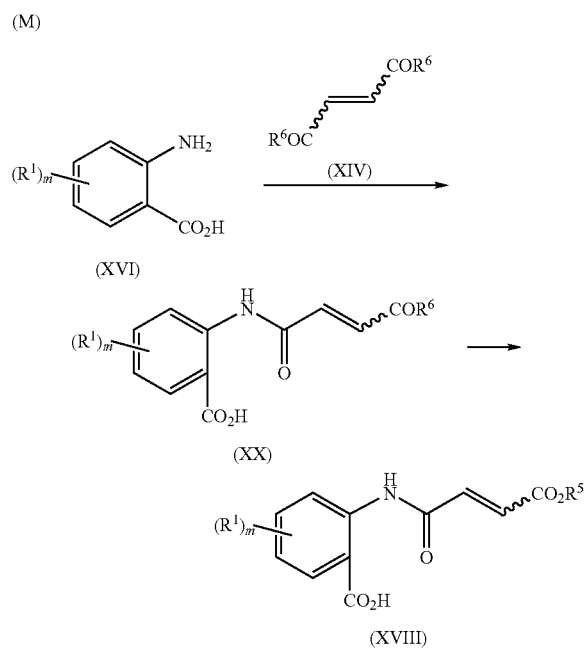

wherein $R^6$ is a chlorine atom or a bromine atom, and $R^1$, $R^5$ and m are as defined above. The compounds of the formulae (XIV), (XVIII) and (XX) have cis- and trans-isomers, and each compound may be any one of such isomers or a mixture thereof.

The first step reaction of the reaction [M] can be carried out usually by treating the compound of the formula (XVI) with the compound of the formula (XIV) in the presence of a solvent. The compound of the formula (XIV) can be used in an amount of from 0.9 to 3 times by mol, preferably from 1 to 1.5 times by mol to the compound of the formula (XVI).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The present reaction may be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; alkali metal alkoxides such as sodium t-butoxide and potassium t-butoxide, and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the compound of the formula (XVI).

The present reaction can be carried out usually at from −10 to 150° C., preferably at from 0 to 50° C., and the reaction time is usually from about 0.5 to about 24 hours.

The second step reaction of the reaction [M] can be carried out usually by treating the compound of the formula (XX) with an alcohol represented by $R^5$—OH in an equimolar amount or more in the presence of a solvent. In the formula, $R^5$ is as defined above.

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The present reaction may be carried out in the presence of a base if desired. As the base, for example, one or more types may suitably be selected from, for example, inorganic bases such as sodium hydroxide, potassium hydroxide, sodium hydride, potassium hydride, sodium carbonate and potassium carbonate; alkali metal alkoxides such as sodium t-butoxide and potassium t-butoxide, and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 2.5 times by mol to the compound of the formula (XX).

The present reaction can be carried out usually at from −10 to 150° C., preferably at from 0 to 50° C., and the reaction time is usually from about 0.5 to about 24 hours.

The compound of the formula (II) including the compound of the above formula (II-1) can be produced in accordance with the following reactions [N] to [Q]:

[N]

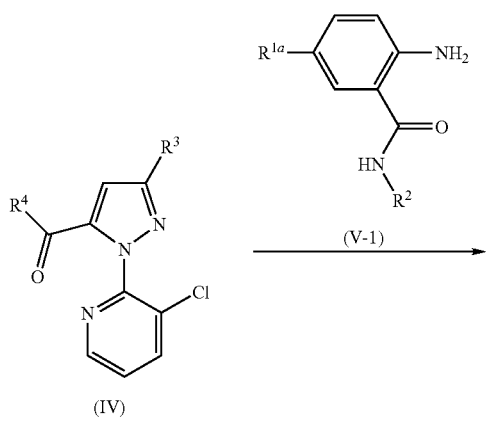

(IV)

(V-1)

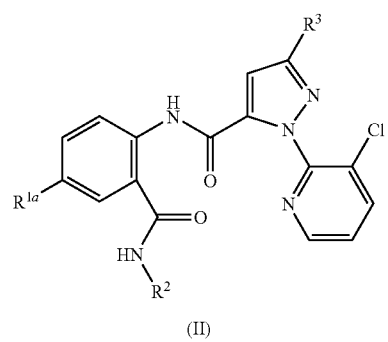

(II)

wherein $R^{1a}$, $R^2$, $R^3$ and $R^4$ are as defined above.

The compound of the formula (IV) which can be used in the above reaction may, for example, be pentyl 3-bromo-1-(3-chloropyridin-2-yl)-1H-pyrazole-5-carboxylate, pentyl 3-chloro-1-(3-chloropyridin-2-yl)-1H-pyrazole-5-carboxylate, phenyl 3-bromo-1-(3-chloropyridin-2-yl)-1H-pyrazole-5-carboxylate or S-benzyl 3-bromo-1-(3-chloropyridin-2-yl)-1H-pyrazole-5-carbothioate.

The compound of the formula (V-1) may, for example, be 2-amino-5-chloro-N-(1-cyclopropylethyl)benzamide, 2-amino-5-chloro-N-(cyclopropylmethyl)benzamide or 2-amino-5-chloro-3-trifluoromethyl-N-(1-cyclopropylethyl)benzamide.

The reaction [N] can be carried out usually by treating the compound of the formula (IV) with the compound of the formula (V-1) in the presence of a base and a solvent.

As the base, one or more types may suitably be selected from, for example, alkali metal hydrides such as sodium hydride and potassium hydride; alkali metal carbonates such as sodium carbonate and potassium carbonate, alkali metal alkoxides such as sodium methoxide, sodium ethoxide and potassium tert-butoxide; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.5 to 5 times by mol, preferably from 1 to 3 times by mol to the compound (V-1).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

A dehydrating agent may be added to the reaction system so as to prevent hydrolysis during the reaction. The dehydrating agent may, for example, be anhydrous sodium sulfate or anhydrous magnesium sulfate, and it can be added in an amount of from 1 to 100 times by mol to the compound (V-1).

The reaction [N] can be carried out usually at from 0 to 120° C., preferably at from 5 to 80° C., and the reaction time is usually from about 0.25 to about 24 hours, preferably from about 0.5 to about 12 hours.

In the above reaction, the compound of the formula (II-1) can be produced from a compound of the formula (IV-1):

[N-1]

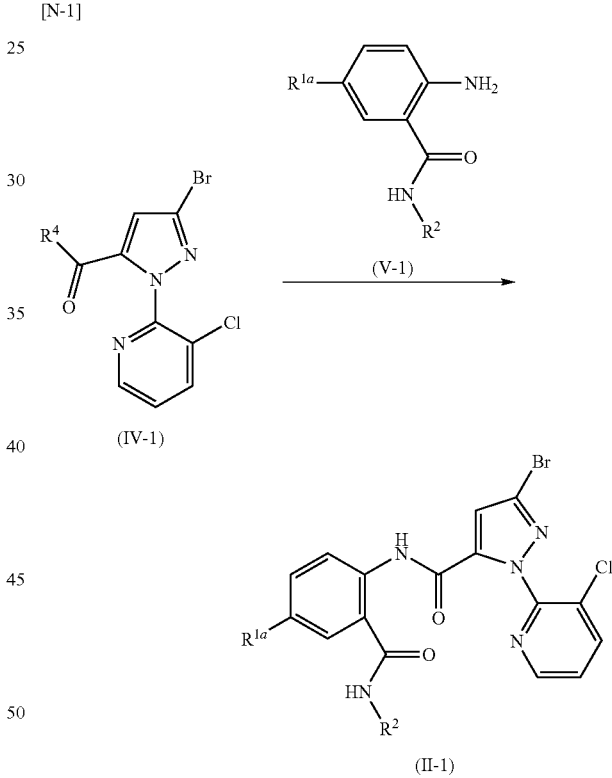

wherein $R^{1a}$, $R^2$ and $R^4$ are as defined above.

The compound of the formula (IV-1) which can be used in the above reaction may, for example, be pentyl 3-bromo-1-(3-chloropyridin-2-yl)-1H-pyrazole-5-carboxylate, phenyl 3-bromo-1-(3-chloropyridin-2-yl)-1H-pyrazole-5-carboxylate or S-benzyl 3-bromo-1-(3-chloropyridin-2-yl)-1H-pyrazole-5-carbothioate.

A compound of the formula (IV-2) which is the compound of the formula (IV) to be used in the reaction [N] wherein $R^4$ is $C_{5-10}$ alkyloxy, substitutable phenoxy or substitutable benzyloxy can be produced in accordance with the following reaction [O]:

[O]

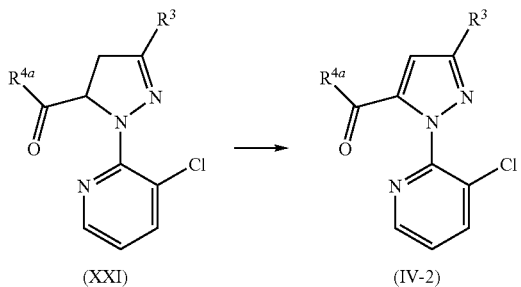

wherein $R^{4a}$ is $C_{5-10}$ alkyloxy, substitutable phenoxy or substitutable benzyloxy, and $R^3$ is as defined above.

The reaction [O] can be carried out usually by treating the compound of the formula (XXI) with an oxidizing agent in the presence of an acid and a solvent.

The oxidizing agent may, for example, be hydrogen peroxide, potassium persulfate, sodium persulfate, potassium peroxymonosulfate or potassium permanganate, and one or more types may suitably be selected. The oxidizing agent may be used in an amount of from 1 to 5 times by mol, preferably from 1 to 2.5 times by mol to the compound (XXI).

The acid may, for example, be sulfuric acid, phosphoric acid or acetic acid. The acid may be used in an amount of from 0.5 to 5 times by mol to the compound (XXI).

The solvent may be any solvent so long as it is inert to the reaction. For example, one or more types may suitably be selected from, for example, ethers such as tetrahydrofuran, dioxane and dimethoxyethane; ketones such as acetone and methyl ethyl ketone; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; polar aprotic solvents such as acetonitrile, propionitrile, N,N-dimethylformamide, dimethyl sulfoxide, hexamethylphosphoric triamide, sulfolane, dimethylacetamide and N-methylpyrrolidone, and water.

The reaction [O] can be carried out usually at from 0 to 150° C., preferably at from 15 to 120° C., and the reaction time is usually from about 0.5 to about 24 hours, preferably from about 1 to about 4 hours.

A compound of the formula (XXI-1) which is the compound (XXI) to be used in the reaction [O] wherein $R^3$ is a chlorine atom or a bromine atom can be produced in accordance with the following reaction [P]:

[P]

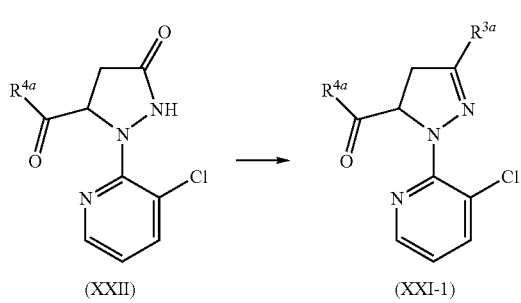

wherein $R^{3a}$ is a chlorine atom or a bromine atom, and $R^{4a}$ is as defined above.

The reaction [P] can be carried out usually by treating the compound of the formula (XXII) with a halogenating agent in the presence of a solvent.

As the halogenating agent, phosphorus oxyhalide such as phosphorus oxybromide or phosphorus oxychloride may be used. The halogenating agent can be used in an amount of from 0.33 to 3 times by mol, preferably from 0.5 to 2 times by mol to the compound of the formula (XXII).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The reaction [P] can be carried out usually at from 0 to 120° C., preferably at from 5 to 100° C., and the reaction time is usually from about 0.2 to about 8 hours, preferably from about 0.5 to about 4 hours.

The compound (XXII) can be prepared in accordance with the following reaction [Q]:

[Q]

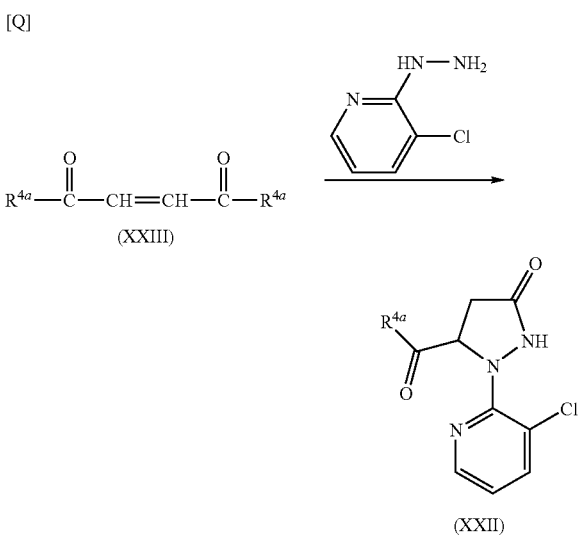

wherein $R^{4a}$ is as defined above.

The reaction [Q] can be carried out usually by treating 3-chloro-2-hydrazinylpyridine with a fumarate or a maleate or a mixture thereof in the presence of a base and a solvent.

As the base, an alkali metal alkoxide such as sodium pentoxide or potassium pentoxide may be used. Such an alkali metal alkoxide can be prepared from an alkali metal hydride such as sodium hydride or potassium hydride; an alkali metal hydroxide such as sodium hydroxide or potassium hydroxide and an alkali metal such as sodium or potassium, and an alcohol. The base can be used in an amount of from 0.7 to 3 times by mol, preferably from 1 to 1.5 times by mol to 3-chloro-2-hydrazinylpyridine.

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; and alcohols such as 1-pentanol, 2-pentanol and 1-hexanol. An alcohol is preferred, and particularly preferred is the same alcohol as one constituting the fumarate or the maleate and the alkoxide base.

The reaction [Q] can be carried out usually at from 0 to 150° C., preferably at from 20 to 130° C., and the reaction time is usually from about 0.5 to about 24 hours, preferably from about 1 to about 4 hours.

Further, the compound represented by the above formula (I) can be produced also in accordance with the following reaction [R] and a conventional process for producing a salt:

[R]

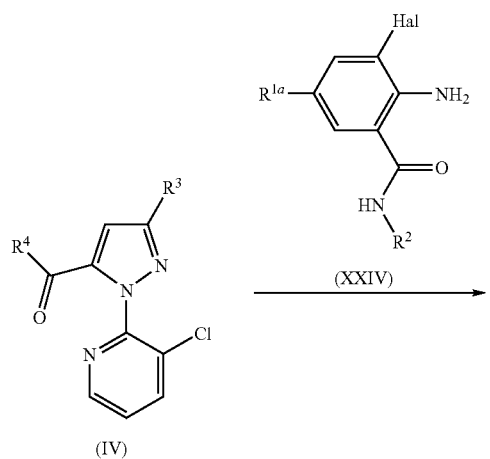

(IV)

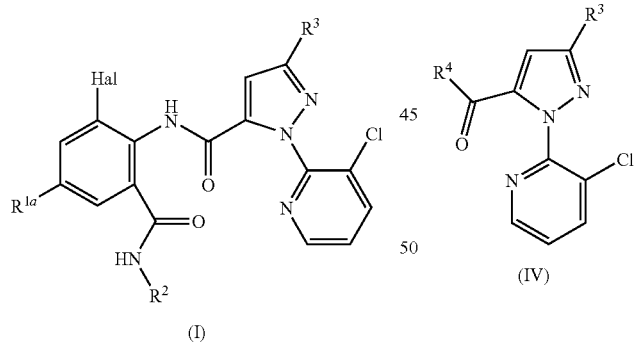

(I)

wherein $R^{1a}$, $R^2$, $R^3$, $R^4$ and Hal are as defined above.

The reaction [R] can be carried out usually by treating the compound of the formula (IV) with the compound of the formula (XXIV) in the presence of a base and a solvent.

As the base, one or more may suitably be selected from, for example, alkali metal hydrides such as sodium hydride and potassium hydride; alkali metal carbonates such as sodium carbonate and potassium carbonate, alkali metal alkoxides such as sodium methoxide, sodium ethoxide and potassium tert-butoxide; and tertiary amines such trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.5 to 5 times by mol, preferably from 1 to 3 times by mol to the compound (IV).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

A dehydrating agent may be added to the reaction system so as to prevent hydrolysis during the reaction. The dehydrating agent may, for example, be anhydrous sodium sulfate or anhydrous magnesium sulfate, and it can be added in an amount of from 1 to 100 times by mol to the compound (XXIV).

The reaction [R] can be carried out usually at from 0 to 120° C., preferably at from 5 to 80° C., and the reaction time is usually from about 0.5 to about 24 hours, preferably from about 1 to about 12 hours.

Further, in accordance with the reaction [R], a compound of the formula (I-B) can be produced in accordance with the reaction [S]:

[S]

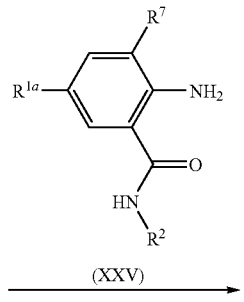

(IV)

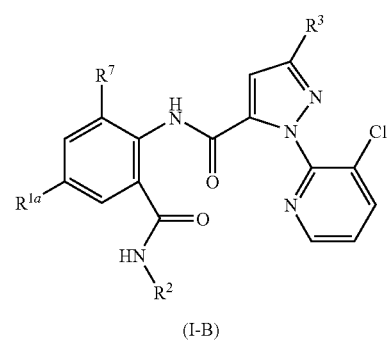

(I-B)

wherein $R^7$ is a hydrogen atom, halogen, alkyl or haloalkyl, and $R^{1a}$, $R^2$, $R^3$ and $R^4$ are as defined above.

The reaction [S] can be carried out usually by treating the compound of the formula (IV) with the compound of the formula (XXV) in the presence of a base and a solvent.

As the base, one or more may suitably be selected from, for example, alkali metal hydrides such as sodium hydride and potassium hydride; alkali metal carbonates such as sodium carbonate and potassium carbonate, alkali metal alkoxides such as sodium methoxide, sodium ethoxide and potassium tert-butoxide; and tertiary amines such trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.5 to 5 times by mol, preferably from 1 to 3 times by mol to the compound (IV).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

A dehydrating agent may be added to the reaction system so as to prevent hydrolysis during the reaction. The dehydrating agent may, for example, be anhydrous sodium sulfate or anhydrous magnesium sulfate, and it can be added in an amount of from 1 to 100 times by mol to the compound (XXV).

The reaction [S] can be carried out usually at from 0 to 120° C., preferably at from 5 to 80° C., and the reaction time is usually from about 0.5 to about 24 hours, preferably from about 1 to about 12 hours.

The compound (IV) can be produced in accordance with the following reaction [T]:

[T]

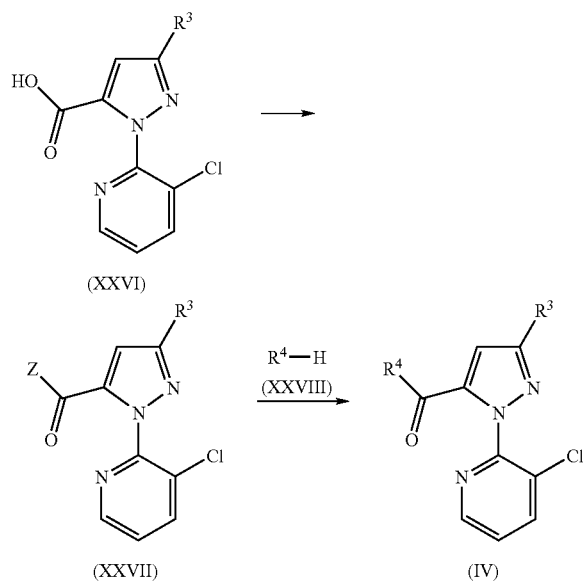

wherein Z is a chlorine atom, a methoxycarbonyloxy group, an ethoxycarbonyloxy group, a methylsulfonyloxy group, a phenylsulfonyloxy group or a p-toluenesulfonyloxy group, and $R^3$ and $R^4$ are as defined above.

The first step of the reaction [T] can be carried out by treating the compound of the formula (XXVI) with a chlorinating agent, an acid chloride or the like in an equimolar amount or more.

The chlorinating agent may, for example, be thionyl chloride, oxalyl dichloride, phosphorus trichloride or phosphorus pentachloride. The acid chloride may, for example, be methyl chlorocarbonate, ethyl chlorocarbonate, methylsulfonyl chloride, phenylsulfonyl chloride or p-toluenesulfonyl chloride.

In this reaction, a solvent may be use, and the solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; and polar aprotic solvents such as acetonitrile, propionitrile and N,N-dimethylformamide.

The first step of the reaction [T] can be carried out usually at from −20 to 140° C., preferably from −10 to 120° C., and the reaction time is usually from about 0.1 to about 10 hours, preferably from about 0.5 to about 5 hours.

In a case where in the compound of the formula (XXVII) Z is an alkoxycarbonyloxy group, a methylsulfonyloxy group, a phenylsulfonyloxy group or a p-toluenesulfonyloxy group, the first step may be carried out also in the presence of a base.

As the base, for example, one or more types may suitably be selected from, for example, alkali metal carbonates such as sodium carbonate and potassium carbonate; alkali metal hydrides such as sodium hydride and potassium hydride; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 1 to 5 times by mol, preferably from 1 to 2.5 times by mol to the compound of the formula (XXVI).

The second step of the reaction [T] can be carried out usually by treating the compound of the formula (XXVII) with the compound of the formula (XXVIII) in the presence of a base and a solvent.

As the base, one or more may suitably be selected from, for example, alkali metal hydrides such as sodium hydride and potassium hydride; alkali metal carbonates such as sodium carbonate and potassium carbonate, alkali metal alkoxides such as sodium methoxide, sodium ethoxide and potassium tert-butoxide; and tertiary amines such trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.8 to 3 times by mol, preferably from 1 to 1.5 times by mol to the compound (XXVIII).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; alcohols such as pentanol, hexanol and isoamyl alcohol, and water. The alcohol such as pentanol, hexanol or isoamyl alcohol is one example of the compound (XXVIII) and the reaction reagent can be utilized also as the solvent.

The second step of the reaction [T] can be carried out usually at from −20 to 120° C., preferably from 0 to 40° C., and the reaction time is usually from about 0.25 to 24 hours, preferably from about 0.5 to about 12 hours.

The compound (XXVI) is a known compound disclosed in e.g. WO03/016283 obtainable by hydrolysis of the compound of the formula (IV), and one skilled in the art can obtain it by a known method. The compound of the formula (XXVIII) is also a known compound which is commercially available and is readily available.

The compound of the formula (V-1) to be used in the above reactions [H] and [N] and the compound of the formula (XXIV) to the used in the above reaction [R] can be produced in accordance with the following reaction [U]:

[U]

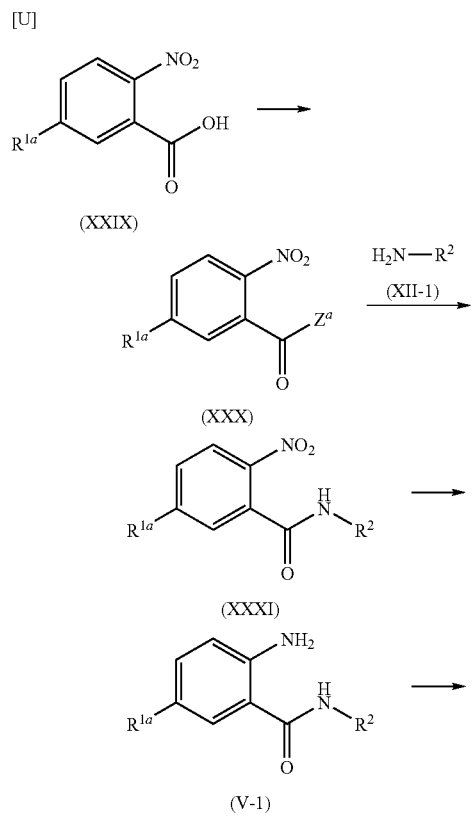

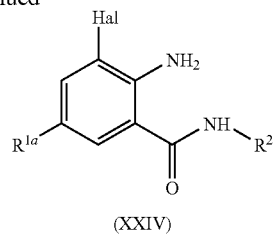

wherein $Z^a$ is a chlorine atom, a methoxycarbonyloxy group, an ethoxycarbonyloxy group or a p-toluenesulfonyloxy group, and $R^{1a}$, $R^2$ and Hal are as defined above.

The first step of the reaction [U] can be carried out by reacting the compound (XXIX) with a chlorinating agent, an acid chloride or the like in an equimolar amount or more.

The chlorinating agent may, for example, be thionyl chloride, oxalic dichloride, phosphorus trichloride or phosphorus pentachloride. The acid chloride may, for example, be methyl chlorocarbonate or ethyl chlorocarbonate.

In this reaction, a solvent may be use, and the solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; and polar aprotic solvents such as acetonitrile, propionitrile and N,N-dimethylformamide.

The first step of the reaction [U] can be carried out usually at from −20 to 140° C., preferably from −10 to 120° C., and the reaction time is usually from about 0.1 to about 10 hours, preferably from about 0.5 to about 5 hours.

In a case where in the compound of the formula (XXX) $Z^a$ is a methoxycarbonyloxy group or an ethoxycarbonyloxy group, the first step may be carried out also in the presence of a base.

As the base, for example, one or more types may suitably be selected from, for example, alkali metal carbonates such as sodium carbonate and potassium carbonate; alkali metal hydrides such as sodium hydride and potassium hydride; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 1 to 5 times by mol, preferably from 1 to 2.5 times by mol to the compound of the formula (XXIX).

The second step of the reaction [U] can be carried out usually by reacting the compound of the formula (XXX) with a substituted amine (XII-1) in an equimolar amount or more in the presence of a solvent.

The solvent may be any solvent so long as it is inert to the reaction. For example, one or more types may suitably be selected from, for example, ethers such as diethyl ether, butyl ethyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene;

aromatic hydrocarbons such as benzene, toluene and xylene; aliphatic hydrocarbons such as pentane, hexane, heptane, octane and cyclohexane; esters such as methyl acetate, ethyl acetate and propyl acetate; and polar aprotic solvents such as acetonitrile, propionitrile and N,N-dimethylformamide.

The second step of the reaction [U] can be carried out usually at from −10 to 100° C., preferably from 0 to 50° C., and the reaction time is usually from about 0.1 to about 24 hours, preferably from about 0.5 to about 12 hours.

The second step of the reaction [U] may be carried out also in the presence of a base.

As the base, for example, one or more types may suitably be selected from, for example, alkali metal carbonates such as sodium carbonate and potassium carbonate; alkali metal hydrides such as sodium hydride and potassium hydride; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 1 to 5 times by mol, preferably from 1 to 2.5 times by mol to the compound of the formula (XXX).

The third step of the reaction [U] can be carried out usually by subjecting the compound of the formula (XXXI) to catalytic hydrogenation by a metal catalyst in hydrogen atmosphere under normal pressure to several atmospheres in the presence of a solvent or by reacting the compound of the formula (XXXI) with a metal catalyst in an acidic solvent for reduction. As the metal catalyst, for example, one or more types may suitably be selected from, for example, palladium carbon, platinum oxide, Raney Nickel, iron or stannic chloride.

Hydrogen in the third step of the reaction [U] can be used in amount of from 1 to 200 times by mol, preferably from 1 to 50 times by mol to the compound of the formula (XXXI).

The solvent may be any solvent so long as it is inert to the reaction. For example, one or more types may suitably be selected from, for example, water, acetic acid, ethyl acetate; alcohols such as methanol, ethanol, propanol, n-butanol and tert-butanol; ethers such as diethyl ether, butyl methyl ether, tetrahydrofuran, dioxane and dimethoxyethane; aromatic hydrocarbons such as benzene, toluene and xylene; and aliphatic hydrocarbons such as pentane, hexane, heptane, octane and cyclohexane.

The third step of the reaction [U] can be carried out usually at from −10 to 100° C., preferably at from 0 to 80° C., and the reaction time is usually from about 0.5 to about 24 hours, preferably from about 1 to about 12 hours.

The fourth step of the reaction [U] can be carried out usually by treating the compound of the formula (V-1) with a halogenating agent in the presence of a solvent. Further, in a case where chlorine or bromine is used as the halogenating agent, it can be carried out in the presence of a base and a solvent.

The halogenating agent can be selected from chlorine, bromine, N-bromosuccinimide and N-chlorosuccinimide.

As the base, one or more types may suitably be selected from, for example, metal hydroxides such as sodium hydroxide, lithium hydroxide, potassium hydroxide and calcium hydroxide, alkali metal hydrides such as sodium hydride and potassium hydride, and alkali metal alkoxides such as sodium methoxide, sodium ethoxide and potassium tert-butoxide. The base can be used in an amount of from 0.8 to 5 times by mol, preferably from 1 to 3 times by mol to the compound (V-1).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; and alcohols such as methanol, ethanol, propanol, n-butanol and tert-butanol.

The fourth step of the reaction [U] can be carried out usually at from −20 to 120° C., preferably at from 0 to 80° C., and the reaction time is usually from about 0.5 to about 24 hours, preferably from about 1 to about 12 hours.

Further, the compound (V-1) wherein $R^{1a}$ is a chlorine atom or a bromine atom can be produced also in accordance with the following reaction [V]:

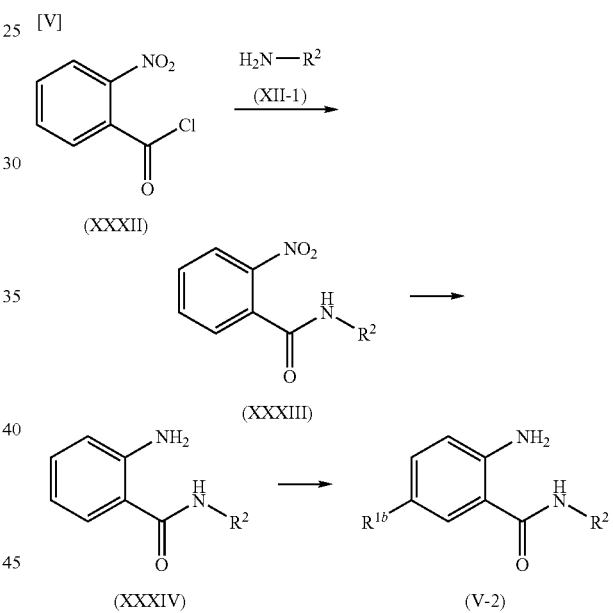

wherein $R^{1b}$ is a chlorine atom or a bromine atom, and $R^2$ is as defined above.

The first step of the formula [V] can be carried out in the same manner as the second step of the above reaction [U]. Namely, the compound (XXXIII) can be obtained usually by reacting the compound (XXXII) with a substituted amine (XII-1) in an equimolar amount or more in the presence of a solvent.

The second step of the formula [V] can be carried out in the same manner as the third step of the above reaction [U]. Namely, the compound (XXXIV) can be prepared usually by subjecting the compound (XXXIII) to catalytic hydrogenation by a metal catalyst in hydrogen atmosphere under normal pressure to several atmospheres in the presence of a solvent or by reacting the compound (XXXIII) with a metal catalyst in an acidic solvent for reduction.

The third step of the reaction [V] can be carried out by reacting the compound (XXXIV) with a halogenating agent usually in the presence of a solvent.

The halogenating agent may suitably be selected from, for example, halogens such as chlorine or bromine; active halogenating agents such as trichloroisocyanuric acid, N-chlorosuccinimide and N-bromosuccinimide; and a mixed aqueous solution of hydrogen peroxide with hydrogen chloride or hydrogen bromide.

The solvent is any solvent so long as it is inert to the reaction. For example, one or more types may suitably be selected from, for example, ethers such as diethyl ether, butyl methyl ether, tetrahydrofuran, dioxane and dimethoxyethane; esters such as methyl acetate, ethyl acetate and propyl acetate; and polar aprotic solvents such as acetonitrile, propionitrile and N,N-dimethylformamide.

The third step of the reaction [V] can be carried out usually at from −10 to +100° C., preferably at from 0 to 50° C., and the reaction time is usually from about 0.1 to 12 hours, preferably from about 0.5 to about 6 hours.

The cycloalkylalkylamine such as the compound (XII-1) to be used in the above reactions [U] and [V] is a known compound, and can be produced by a method disclosed in J. Am. Chem. Soc., 1966, vol. 88, p. 2267 or in accordance with known literature such as J. Med. Chem., 1997, vol. 40, p. 3215. Further, the compound of the formula (XXXVII) can be produced also by a method (Leuckart method) disclosed in Eur. J. Med. Chem., 2001, p. 265 to 286 or by the following reaction [W] in accordance with the above method:

[W]

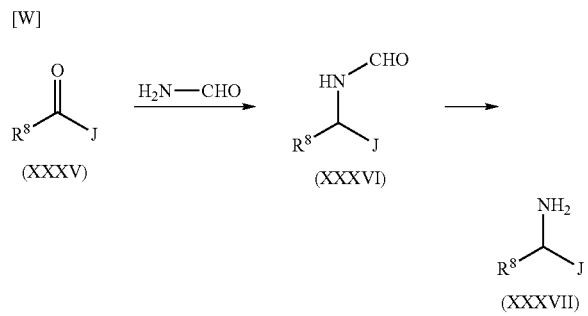

wherein $R^8$ is cyclopropyl, cyclopropylalkyl, cyclobutyl or cyclobutylalkyl, and J is hydrogen or alkyl.

The first step of the reaction [W] can be carried out by reacting the compound of the formula (XXXV) with formamide in the presence of an acid.

As the solvent, formamide is used, and any solvent can be used together with formamide so long as it is inert to the reaction. For example, one or more types may suitably be selected from, for example, ethers such as diethyl ether, butyl ethyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; alcohols such as methanol, ethanol, propanol, n-butanol and tert-butanol, and water.

As the acid, one or more types may suitably be selected from, for example, organic acids such as formic acid, a $C_{1-6}$ alkyl carboxylic acid, an aromatic carboxylic acid, a $C_{1-6}$ alkyl sulfonic acid and an aromatic sulfonic acid; amine hydrochlorides such as ammonium chloride, trimethylamine hydrochloride, triethylamine hydrochloride, pyridine hydrochloride, 4-dimethylaminopyridine hydrochloride, 2,6-dimethylpyridine hydrochloride, 4-pyrrolidinopyridine hydrochloride, N-methylmorpholine hydrochloride and N,N-dimethylaniline hydrochloride; Lewis acids such as titanium halide, aluminum halide, iron halide, tin halide, zinc halide, magnesium halide, silicon halide, copper halide and trifluoroborane-ether complex. The acid can be used in an amount of from 0.05 to 10 times by mol, preferably from 0.1 to 5 times by mol to the compound (XXXV).

The first step of the reaction [W] can be carried out usually at from 0 to 200° C., preferably at from 30 to 180° C., and the reaction time is usually from about 1 to about 24 hours, preferably from about 2 to about 12 hours.

The second step of the reaction [W] can be carried out usually by subjecting the compound of the formula (XXXVI) to hydrolysis using an acid or a base in the presence of a solvent. As the acid, one or more types may suitably be selected from, for example, hydrogen halides such as hydrogen chloride, hydrogen bromide, hydrogen iodide and hydrogen fluoride; inorganic acids such as sulfuric acid, sulfurous acid, nitric acid, nitrous acid, phosphoric acid, boric acid, chloric acid, chlorous acid and hypochlorous acid; Lewis acids such as titanium halide, aluminum halide, iron halide, tin halide, zinc halide, magnesium halide, silicon halide, copper halide and trifluoroborane-ether complex; and organic acids such as formic acid, $C_{1-6}$ alkyl carboxylic acid, aromatic carboxylic acid, $C_{1-6}$ alkyl sulfonic acid and aromatic sulfonic acid.

As the base, one or more types may suitably be selected from, for example, alkali metal hydroxides such as sodium hydroxide and potassium hydroxide; alkali metal hydrides such as sodium hydride and potassium hydride; alkali metal carbonates such as sodium carbonate and potassium carbonate, and alkali metal alkoxides such as sodium methoxide, sodium ethoxide and potassium tert-butoxide. The acid or the base can be used in an amount of from 0.1 to 5 times by mol, preferably from 1 to 2.5 times by mol to the compound (XXXVI). The solvent in this case may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; polar solvents such as acetonitrile, propionitrile, N,N-dimethylformamide, N-methylformamide, formamide, dimethyl sulfoxide, hexamethylphosphoric triamide, sulfolane, dimethylacetamide, N-methylpyrrolidone, formic acid, acetic acid, propionic acid and butyric acid; alcohols such as methanol, ethanol, propanol, n-butanol and tert-butanol, and water.

The second step of the reaction [W] can be carried out usually at from −10 to 150° C., preferably at from 0 to 100° C., and the reaction time is usually from about 0.1 to about 10 hours, preferably from about 0.5 to about 2 hours.

The compound of the above formula (XXXVII) can be taken out as a salt by adding an acid such as hydrogen chloride, hydrochloric acid or sulfuric acid to the reaction liquid during the production process.

Further, the compound (XXXVII) can be produced also in accordance with the following process:

[X]

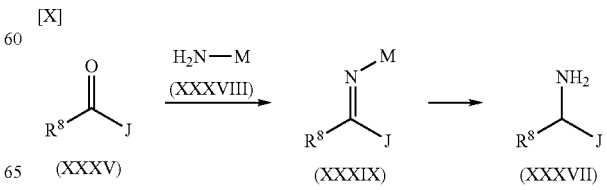

wherein $R^8$ and J are as defined above, M is —OH or —OG (G is an ether residue), and G is, for example, a $C_{1-6}$ alkyl such as methyl or ethyl or phenyl which may be substituted by a $C_{1-6}$ alkyl.

The first step of the reaction [X] can be carried out usually by reacting the compound (XXXV) with the compound (XXXVIII) in the presence of a solvent.

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; alcohols such as methanol, ethanol, propanol, n-butanol and tert-butanol, and water.

The first step of the reaction [X] can be carried out usually at from 0 to 150° C., preferably at from 30 to 110° C., and the reaction time is usually from about 0.5 to about 24 hours, preferably from about 1 to about 12 hours.

The second step of the reaction [X] can be carried out usually by reducing the compound of the formula (XXXIX) using a reducing agent in the presence of a solvent.

As the reducing agent, for example, one or more types may suitably be selected from, for example, lithium aluminum hydride and sodium borohydride. In a case where sodium borohydride is used as the reducing agent, a Lewis acid such as molybdenum trioxide, titanium tetrachloride, cobalt chloride or nickel chloride may be added so as to increase reactivity.

The solvent in this case may be any solvent so long as it is inert to the reaction. For example, one or more types may suitably be selected from, for example, ethers such as diethyl ether, butyl methyl ether, tetrahydrofuran, dioxane and dimethoxyethane.

Further, the second step of the reaction [X] can also be carried out usually by reducing the compound of the formula (XXXIX) by catalytic hydrogenation with a metal catalyst in hydrogen atmosphere under normal pressure to several atmospheres in the presence of a solvent. As the metal catalyst, for example, one or more types may suitably be selected from, for example, palladium carbon, platinum oxide and Raney nickel.

The solvent in this case may be any solvent so long as it is inert to the reaction. For example, one or more types may suitably be selected from, for example, water, acetic acid, ethyl acetate; alcohols such as methanol, ethanol, propanol, n-butanol and tert-butanol; ethers such as diethyl ether, butyl methyl ether, tetrahydrofuran, dioxane and dimethoxyethane; aromatic hydrocarbons such as benzene, toluene and xylene; and aliphatic hydrocarbons such as pentane, hexane, heptane, octane and cyclohexane.

The second step of the reaction [X] can be carried out usually at from –10 to 100° C., preferably at from 0 to 80° C., and the reaction time is usually from about 0.5 to about 24 hours, preferably from about 2 to about 12 hours.

The compounds obtained by the above-described reactions [A] to [X] may have optical isomers or geometrical isomers in some cases, and such isomers and mixtures thereof are both included in the present invention. Further, in the present invention, various isomers other than those mentioned above may be included within the scope of the common knowledge in this technical field. Further, depending upon the type of such an isomer, the chemical structure may be different from the structures in the above reaction formulae, but it is obvious to one skilled in the art that such a structure is in isomeric relation and thus falls within the scope of the present invention.

Further, the present invention includes the following processes.

(1) A process for producing the compound of the formula (II-1) by the above reaction [B-1].

(2) A process for producing the compound of the formula (III-1) by the above reaction [C-1].

(3) A process for producing the compound of the formula (IX-1) by the above reaction [D-1].

(4) A process for producing the compound of the formula (VIII-1) by the above reaction [E-1].

(5) A process for producing the compound of the formula (VI-1) by the above reaction [F-1].

(6) A process for producing the compound of the formula (X-1) by the above reaction [G-1].

(7) A process for producing the compound of the formula (II-1) and producing the compound of the formula (I-1) by the above reactions [B-1] and [A-1].

(8) A process for producing the compound of the formula (VIII-1), producing the compound of the formula (IX-1), producing the compound of the formula (III-1) and producing the compound of the formula (II-1) by the above reactions [E-1], [D-1], [C-1] and [B-1].

(9) A process for producing the compound of the formula (VIII-1), producing the compound of the formula (IX-1), producing the compound of the formula (III-1), producing the compound of the formula (II-1) and producing the compound of the formula (I-1) by the above reactions [E-1], [D-1], [C-1], [B-1] and [A-1].

(10) A process for producing the compound of the formula (VI-1), producing the compound of the formula (VIII-1), producing the compound of the formula (IX-1), producing the compound of the formula (III-1) and producing the compound of the formula (II-1) by the above reactions [F-1], [E-1], [D-1], [C-1] and [B-1].

(11) A process for producing the compound of the formula (X-1), producing the compound of the formula (VI-1), producing the compound of the formula (VIII-1), producing the compound of the formula (IX-1), producing the compound of the formula (III-1) and producing the compound of the formula (II-1) by the above reactions [G-1], [F-1], [E-1], [D-1], [C-1] and [B-1].

(12) A process for producing the compound of the formula (II-1) by the above reaction [N-1].

(13) A process for producing the compound of the formula (II-1) and producing the compound of the formula (I-1) by the above reactions [N-1] and [A-1].

EXAMPLES

Now, the present invention will be described in detail with reference to Examples, but it should be understood that the present invention is by no means restricted thereto.

Example 1

Preparation (1) of methyl (E)-3-(6-chloro-4-oxo-4H-benzo[d][1,3]oxazin-2-yl)acrylate A mixed solution comprising 1.49 g of methanesulfonyl chloride and 10 ml of acetonitrile was cooled with ice, and 10 ml of an acetonitrile solution comprising 1.3 g of monomethyl maleate and 1.34 g of pyridine was dropwise added thereto under cooling with ice over a period of 5 minutes, followed by stirring for 5 minutes at the same temperature. 10 ml of an acetonitrile solution comprising 1.72 g of 5-chloroanthranilic acid and 2.77 g of pyridine was added under cooling with ice over a period of 2 minutes, followed by rinsing with 5 ml of acetonitrile and stirring for 20 minutes at the same temperature. 1.49 g of methanesulfonyl chloride was added over a period of 2 minutes under cooling with ice, followed by rinsing with 2 ml of acetonitrile and stirring for 30 minutes, and then the temperature was returned to room temperature, followed by reaction for 4 hours. The reaction liquid was poured to 20 ml of water, followed by stirring for 30 minutes. The resulting crystals were collected by filtration, washed with water and a mixed liquid of acetonitrile:water (2:1), and dried to obtain 1.82 g of the brown desired product (melting point: 162 to 164° C.).

$^1$H-NMR (400 MHz, CDCl$_3$) δ: 8.20 (dd, 1H), 7.77 (dd, 1H), 7.61 (dd, 1H), 7.23 (d, 1H), 7.01 (d, 1H), 3.84 (s, 3H)

Example 2

Preparation (2) of methyl (E)-3-(6-chloro-4-oxo-4H-benzo[d][1,3]oxazin-2-yl)acrylate (1) Preparation of (Z)-5-chloro-2-(4-methoxy-4-oxo-2-butenamide)benzoic acid 3.7 g of hydrogen chloride gas was absorbed into 120 ml of methanol at room temperature, and 30.2 g of (Z)-2-(3-carboxyacrylamide)-5-chlorobenzoic acid was added, followed by stirring for 2 hours at from 30 to 35° C. 150 ml of water was added to the reaction liquid, and the precipitated crystals were subjected to suction filtration. The crystals collected after the filtration were washed with water and dried to obtain 25.4 g of the desired product.

(2) Preparation of methyl (E)-3-(6-chloro-4-oxo-4H-benzo[d][1,3]oxazin-2-yl)acrylate 15.2 mL of acetic anhydride and 0.15 mL of concentrated sulfuric acid were added to a mixed solution comprising 15.2 g of (Z)-5-chloro-2-(4-methoxy-4-oxo-2-butenamide)benzoic acid and 61 ml of ethyl acetate, followed by stirring at room temperature for 45 minutes. 0.3 ml of concentrated hydrochloric acid was added, followed by stirring at the same temperature for one hour. The resulting crystals were collected by filtration, washed with ethyl acetate and dried to obtain 13.3 g of the white desired product.

Example 3

Preparation of methyl 4-(4-chloro-2-(1-cyclopropylethylcarbamoyl)phenylamino)-4-oxocrotonate A mixed solution comprising 0.73 g of α-methyl-cyclopropylmethylamine hydrochloride and 0.91 g of triethylamine in 12 ml of acetonitrile was stirred at room temperature for one hour, and 0.53 g of the crude crystals of methyl (E)-3-(6-chloro-4-oxo-4H-benzo[d][1,3]oxazin-2-yl)acrylate obtained in the above step were added at room temperature, followed by reaction at room temperature for 3 hours. Water was added to the reaction liquid, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=9/1 to 8/2) to obtain 0.22 g of the pale yellow desired product (melting point: 154.4° C.)

$^1$H-NMR (400 MHz, CDCl$_3$) δ: 11.62 (br, 1H), 8.69-8.66 (m, 1H), 7.46-7.43 (m, 2H), 7.05 (d, 1H), 6.88 (d, 2H), 6.21 (brd, 1H), 3.80 (s, 3H), 3.53-3.48 (m, 1H), 1.32 (d, 3H), 0.96-0.90 (m, 1H), 0.62-0.48 (m, 2H), 0.42-0.36 (m, 1H), 0.34-0.29 (m, 1H)

Example 4

Preparation (1) of N-(4-chloro-2-(1-cyclopropylethylcarbamoyl)phenyl)-5-oxopyrazolidine-3-carboxamide A mixed liquid comprising 90 mg of hydrazine monohydrate and 3 ml of ethanol was added to a mixed liquid comprising 0.56 g of methyl 4-(4-chloro-2-(1-cyclopropylethylcarbamoyl)phenylamino)-4-oxocrotonate and 3 ml of ethanol, followed by rinsing with 2 ml of ethanol, and reflux under heating for 6 hours. The reaction liquid was stood to cool, the precipitated crystals were subjected to suction filtration, and the obtained crystals were washed with ethanol and air dried to obtain 0.16 g of the desired product (melting point: 248° C.).

$^1$H-NMR (300 MHz, DMSO-d$_6$) δ: 11.83 (s, 1H), 9.14 (d, 1H), 8.53 (d, 1H), 8.36 (dd, 1H), 7.57 (t, 1H), 7.38 (dd, 1H), 5.99 (dd, 1H), 3.99 (t, 1H), 3.30 (m, 1H), 2.56 (dd, 1H), 2.27-2.32 (m, 1H), 1.04 (q, 3H), 0.81 (m, 1H), 0.00-0.40 (m, 4H)

Example 5

Preparation (1) of N-(4-chloro-2-(1-cyclopropylethylcarbamoyl)phenyl)-1-(3-chloropyridin-2-yl)-3-hydroxy-4,5-dihydro-1H-pyrazole-5-carboxamide To a 2-methyl-2-propanol 3 ml mixed liquid comprising 0.10 g of N-(4-chloro-2-(1-cyclopropylethylcarbamoyl)phenyl)-5-oxopyrazolidine-3-carboxamide and 0.09 g of 2,3-dichloropyridine, 15 wt % of palladium-carbon (DeGussa type E105CA/W, manufactured by Aldrich) was added, and then 0.045 g of sodium t-butoxide was added. The mixed liquid was subjected to reaction under reflux for 9 hours. After the reaction liquid was stood to cool, it was poured to a 1 M HCl aqueous solution, followed by extraction with ethyl acetate. The organic layer was washed with a saturated sodium chloride aqueous solution and dried over anhydrous sodium sulfate. The organic layer was subjected to celite filtration, the filtrate was concentrated under reduced pressure, and the residue was purified by silica gel column chromatography (eluent: n-hexane/ethyl acetate=1/0 to 1/1) to obtain 0.11 g of the desired product (melting point: 165 to 167° C.).

$^1$H-NMR (300 MHz, CDCl$_3$) δ: 12.17 (s, 1H), 8.58 (d, 1H), 8.25 (dd, 1H), 7.82 (br, 1H), 7.72 (d, 1H), 7.42 (ds, 2H), 7.10 (dd, 1H), 6.26 (d, 1H), 4.93 (m, 1H), 3.45 (m, 1H), 2.93 (ds, 2H), 1.24 (d, 3H), 0.89 (m, 1H), 0.12-0.64 (m, 4H)

Example 6

Preparation (2) of N-(4-chloro-2-(1-cyclopropylethylcarbamoyl)phenyl)-1-(3-chloropyridin-2-yl)-3-hydroxy-4,5-dihydro-1H-pyrazole-5-carboxamide 1.0 g of N-(4-chloro-2-(1-cyclopropylethylcarbamoyl) phenyl)-5-oxopyrazolidine-3-carboxamide was dissolved in 10 ml of N,N-dimethylformamide, 460 mg of 2,3-dichloropyridine was added and then 350 mg of sodium hydride was added, followed by stirring for about 7 hours at about 70° C. in nitrogen atmosphere, and the reaction liquid was stood to cool. Water was added to the reaction liquid and stirred, followed by extraction with ethyl acetate, and the obtained crude product was purified by silica gel column chromatography (eluent: ethyl acetate/methanol=9/1) to obtain 1.15 g of the desired product.

Example 7

Preparation of 5-(4-chloro-2-(1-cyclopropylethylcarbamoyl)phenylcarbamoyl)-1-(3-chloropyridin-2-yl)-4,5-dihydro-1H-pyrazole-3-yl 4-methylbenzenesulfonate A mixed liquid comprising 2.0 g of N-(4-chloro-2-(1-cyclopropylethylcarbamoyl)phenyl)-1-(3-chloropyridin-2-yl)-3-hydroxy-4,5-dihydro-1H-pyrazole-5-carboxamide and 41 ml of N,N-dimethylformamide was cooled to 0° C., and 0.2 g of sodium hydride (60% oil suspension) was added. After stirring for one hour, 1.2 g of p-toluenesulfonyl chloride was added at 0° C. After stirring for 1.5 hours, the reaction liquid was poured to 120 ml of a 1 M HCl aqueous solution, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/1) to obtain 2.45 g of the desired product in the form of a paste.
$^1$H-NMR (300 MHz, CDCl$_3$) δ: 11.16 (d, 1H), 8.48 (m, 1H), 8.25 (dd, 1H), 8.08 (dd, 1H), 8.00 (d, 2H), 7.61 (d, 1H), 7.36 (m, 4H), 6.83 (m, 1H), 6.04 (t, 1H), 5.49 (ddd, 1H), 3.28-3.46 (m, 3H), 2.45 (s, 3H), 1.23 (dd, 3H), 0.86 (m, 1H), 0.23-0.63 (m, 4H)

Example 8

Preparation (1) of 3-bromo-N-(4-chloro-2-(1-cyclopropylethylcarbamoyl)phenyl)-1-(3-chloropyridin-2-yl)-4,5-dihydro-1H-pyrazole-5-carboxamide 0.54 g of ammonium bromide was added to a mixed liquid comprising 1.0 g of 5-(4-chloro-2-(1-cyclopropylethylcarbamoyl)phenylcarbamoyl)-1-(3-chloropyridin-2-yl)-4,5-dihydro-1H-pyrazol-3-yl 4-methylbenzenesulfonate and 25 ml of N,N-dimethylformamide, followed by heating to 93° C. One hour later, the reaction liquid was poured to 50 ml of water, followed by extraction with diethyl ether. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/1) to obtain 0.11 g of the desired product in the form of a paste.
$^1$H-NMR (300 MHz, CDCl$_3$) δ: 11.48 (d, 1H), 8.50 (dd, 1H), 8.13 (t, 1H), 7.67 (d, 1H), 7.4 (ds, 2E), 6.9 (m, 1H), 6.03 (t, 1H), 5.50 (ddd, 1H), 3.35-3.58 (m, 3H), 1.17 (d, 3H), 0.85 (m, 1H), 0.23-0.6 (m, 4H)

Example 9

Preparation (2) of 3-bromo-N-(4-chloro-2-(1-cyclopropylethylcarbamoyl)phenyl)-1-(3-chloropyridin-2-yl)-4,5-dihydro-1H-pyrazole-5-carboxamide A tetrahydrofuran (1 ml) solution comprising 0.16 g of phosphorus tribromide was dropwise added to a mixed liquid comprising 1.0 g of 5-(4-chloro-2-(1-cyclopropylethylcarbamoyl)phenylcarbamoyl)-1-(3-chloropyridin-2-yl)-4,5-dihydro-1H-pyrazol-3-yl 4-methylbenzenesulfonate and 9 ml of tetrahydrofuran under cooling with ice. After stirring for 5 minutes, the reaction liquid was heated to 45° C. 5 hours later, the reaction liquid was poured to 50 ml of water, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/1) to obtain 0.73 g of the desired product in the form of a paste.

Example 10

Preparation (3) of 3-bromo-N-(4-chloro-2-(1-cyclopropylethylcarbamoyl)phenyl)-1-(3-chloropyridin-2-yl)-4,5-dihydro-1H-pyrazole-5-carboxamide 0.25 g of calcium bromide dihydrate was added to a mixed liquid comprising 1.0 g of 5-(4-chloro-2-(1-cyclopropylethylcarbamoyl)phenylcarbamoyl)-1-(3-chloropyridin-2-yl)-4,5-dihydro-1H-pyrazol-3-yl 4-methylbenzenesulfonate and 10 ml of toluene, followed by heating at about 90° C. for 6.5 hours. After the reaction liquid was stood to cool, 0.41 g of sodium hydrogen carbonate and 10 ml of water were added to the reaction liquid, followed by stirring. After liquid-liquid separation, the organic layer was washed with a saturated sodium chloride aqueous solution and dried over anhydrous sodium sulfate. The solvent was distilled off under reduced pressure to obtain 0.96 g of the crude desired product.

Example 11

Preparation (1) of 3-bromo-N-(4-chloro-2-(1-cyclopropylethylcarbamoyl)phenyl)-1-(3-chloropyridin-2-yl)-1H-pyrazole-5-carboxamide 0.13 g of 3-bromo-N-(4-chloro-2-(1-cyclopropylethylcarbamoyl)phenyl)-1-(3-chloropyridin-2-yl)-4,5-dihydro-1H-pyrazole-5-carboxamide was added to a 1,4-dioxane 6 ml solution comprising 0.14 g of 2,3-dichloro-5,6-dicyano-p-benzoquinone, followed by reflux with heating for 18 hours. After the reaction liquid was stood to cool, it was poured to water, followed by extraction with ethyl acetate, and the organic layer was washed with a saturated sodium chloride aqueous solution and dried over sodium sulfate. The filtrate was distilled under reduced pressure, and the residue was purified by silica gel column chromatography (eluent: n-hexane/ethyl acetate=8/2 to 7/3) to obtain 33 mg of the desired product (melting point: 231 to 233° C.).
$^1$H-NMR (400 MHz, CDCl$_3$) δ: 12.25 (br, 1H), 8.48 (dd, 1H), 8.44 (d, 1H), 7.89 (dd, 1H), 7.45-7.33 (m, 3H), 7.01 (s, 1H), 6.23 (d, 1H), 3.57-3.54 (m, 1H), 1.34 (d, 3H), 0.95-0.90 (m, 1H), 0.63-0.51 (m, 2H), 0.43-0.32 (m, 2H)

Example 12

Preparation (2) of 3-bromo-N-(4-chloro-2-(1-cyclopropylethylcarbamoyl)phenyl)-1-(3-chloropyridin-2-yl)-1H-pyrazole-5-carboxamide 0.24 g of potassium peroxodisulfate and 0.02 g of sulfuric acid were added to a N,N-dimethylformamide 3 ml solution comprising 0.10 g of 3-bromo-N-(4-chloro-2-(1-cyclopropylethylcarbamoyl)phenyl)-1-(3-chloropyridin-2-yl)-4,5-dihydro-1H-pyrazole-5-carboxamide, followed by reflux with heating. 1.5 hours later, the reaction liquid was stood to cool and poured to 10 ml of water, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/2) to obtain 0.09 g of the desired product.

Example 13

Preparation (3) of 3-bromo-N-(4-chloro-2-(1-cyclopropylethylcarbamoyl)phenyl)-1-(3-chloropyridin-2-yl)-1H-pyrazole-5-carboxamide 1.13 g of a 30% hydrogen peroxide solution was added to an ethyl acetate 12 ml solution comprising 0.53 g of 3-bromo-N-(4-chloro-2-(1-cyclopropylethylcarbamoyl)phenyl)-1-(3-chloropyridin-2-yl)-4,5-dihydro-1H-pyrazole-5-carboxamide, followed by reflux with heating. 30 hours later, the reaction liquid was stood to cool and poured to water, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=4/1) to obtain 0.32 g of the desired product.

Example 14

Preparation (1) of 3-bromo-N-[2-bromo-4-chloro-6-[[(1-cyclopropylethyl]amino]carbonyl]phenyl]-1-(3-chloropyridin-2-yl)-1H-pyrazole-5-carboxamide A mixed solution comprising 6.0 g of 3-bromo-N-(4-chloro-2-(1-cyclopropylethylcarbamoyl)phenyl)-1-(3-chloropyridin-2-yl)-1H-pyrazole-5-carboxamide and 75 ml of ethyl acetate was cooled with ice, 1.4 g of sodium hydroxide (flakes) was added, and then 2.8 g of bromine was added over a period of 2 hours. After stirring at room temperature for 18 hours, 60 ml of water was added to the reaction liquid, followed by extraction with ethyl acetate. The organic layer was washed with a sodium chloride aqueous solution and dried over anhydrous sodium sulfate. The solvent was distilled off under reduced pressure, and the precipitated crystals were washed with 20 ml of a mixed solution of ethyl acetate and hexane (1:5) and subjected to filtration to obtain 6.2 g of the desired product in the form of white crystals.

Example 15

Preparation (2) of N-(4-chloro-2-(1-cyclopropylethylcarbamoyl)phenyl)-5-oxopyrazolidine-3-carboxamide (1) Preparation of (Z)-2-(3-carboxyacrylamide)-5-chlorobenzoic acid 150 ml of dioxane was added to 15 g of 5-chloroanthranilic acid and 10.3 g of maleic anhydride, followed reflux with heating. After stirring for 5 hours, the reaction liquid was stood to cool, and the precipitated crystals were subjected to suction filtration. The crystals collected after the filtration were washed with a mixed liquid of hexane:ethyl acetate (3:1) and air dried to obtain 15 g of the pale yellow desired product (melting point: 194.4° C.).
$^{1}$H-NMR (400 MHz, Acetone-d$_{6}$) δ: 11.62 (br, 1H), 8.67 (d, 1H), 8.08 (d, 1H), 7.70 (dd, 1H), 6.67 (d, 1H), 6.39 (d, 1H)

(2) Preparation of (Z)-5-chloro-2-(4-methoxy-4-oxo-2-butenamide)benzoic acid

10 Drops of sulfuric acid were added to a mixed liquid comprising 1.0 g of (Z)-2-(3-carboxyacrylamide)-5-chlorobenzoic acid in 20 ml of methanol, followed by stirring at room temperature for 4.5 hours. Water was added to the reaction liquid, followed by extraction with ethyl acetate, and the organic layer was washed with a saturated sodium chloride aqueous solution and dried over anhydrous sodium sulfate. The solvent was distilled off under reduced pressure to obtain 0.91 g of the desired product (melting point: 136.9° C.).
$^{1}$H-NMR (400 MHz, DMSO-d$_{6}$) δ: 11.17 (s, 1H), 8.44 (d, 1H), 7.92 (d, 1H), 7.68 (dd, 1H), 6.65 (d, 1H), 6.43 (d, 1H), 3.64 (s, 3H)

(3) Preparation of methyl (Z)-3-(6-chloro-4-oxo-4H-benzo[d][1,3]oxazin-2-yl)acrylate A mixed liquid comprising 0.35 g of (Z)-5-chloro-2-(4-methoxy-4-oxo-2-butenamide)benzoic acid and 2 ml of acetic anhydride was stirred at room temperature for 30 minutes, and 3 ml of acetic anhydride was further added, followed by reaction at room temperature for 6.5 hours. The reaction liquid was poured to water, followed by extraction with ethyl acetate, and the organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=9/1 to 8/2) to obtain 0.24 g of the desired product (melting point: 117 to 118° C.).
$^{1}$H-NMR (400 MHz, DMSO-d$_{6}$) δ: 8.09 (d, 1H), 7.97 (d, 1H), 7.65 (dd, 1H), 6.80 (d, 1H), 6.59 (d, 1H), 3.76 (s, 3H)

(4) Preparation of N-(4-chloro-2-(1-cyclopropylethylcarbamoyl)phenyl)-5-oxopyrazolidine-3-carboxamide Using (Z)-methyl 3-(6-chloro-4-oxo-4H-benzo[d][1,3]oxazin-2-yl)acrylate obtained in the above step, N-(4-chloro-2-(1-cyclopropylethylcarbamoyl)phenyl)-5-oxopyrazolidine-3-carboxamide can be produced in accordance with the method of the above Preparation Examples 3 and 4.

Example 16

Preparation (3) of N-(4-chloro-2-(1-cyclopropylethylcarbamoyl)phenyl)-5-oxopyrazolidine-3-carboxamide (1) Preparation of 4-(4-chloro-2-cyclopropylethylcarbamoyl)phenylamino-4-oxoisocrotonic acid A mixed liquid comprising 100 g of 2-amino-5-chloro-N-(1-cyclopropylethyl)benzamide and 300 ml of N,N-dimethylformamide was heated to 65° C. 49.5 g of maleic anhydride was added with stirring. One hour later, the reaction liquid was poured to 900 ml of water with stirring. After stirring for 10 minutes, the precipitated crystals were subjected to suction filtration. The crystals collected after the filtration were washed with 250 ml of ethyl acetate and air dried to obtain 135 g of the desired product (melting point: 173° C.).

¹H-NMR (300 MHz, CDCl₃) δ: 12.39 (s, 1H), 8.60 (d, 1H), 7.54 (s, 1H), 7.51 (d, 1H), 6.43 (q, 2H), 6.09 (br, 1H), 3.5 (m, 1H), 1.34 (d, 3H), 0.95 (m, 1H), 0.29-0.69 (m, 4H)

(2) Preparation of methyl 4-(4-chloro-2-(1-cyclopropylethylcarbamoyl)phenylamino)-4-oxoisocrotonate A mixed liquid comprising 97.7 g of 4-(4-chloro-2-cyclopropylethylcarbamoyl)phenylamino)-4-oxoisocrotonic acid in 950 ml of methanol was cooled to 0° C. Sulfuric acid was dropwise added with stirring. The reaction liquid was stirred for 20 hours while the temperature was gradually returned to room temperature. 1.4 L of a saturated sodium chloride aqueous solution was added to the reaction liquid, followed by extraction with ethyl acetate. The organic phase was washed with a saturated sodium chloride aqueous solution and dried over anhydrous sodium sulfate. The solvent was distilled off under reduced pressure to obtain 95.0 g of the desired product (melting point: 131° C.).

¹H-NMR (300 MHz CDCl₃) δ: 11.19 (s, 1H), 8.57 (d, 1H), 7.44 (d, 1H), 7.4 (dd, 1H), 6.38 (br, 1 H), 6.29 (q, 2H), 3.77 (s, 3H), 3.48 (m, 1H), 1.31 (d, 3H), 0.94 (m, 1H), 0.27-0.69 (m, 4H)

(3) Preparation of N-(4-chloro-2-(1-cyclopropylethylcarbamoyl)phenyl)-5-oxopyrazolidine-3-carboxamide 3.58 g of hydrazine monohydrate was dropwise added to a mixed liquid comprising 25 g of methyl 4-(4-chloro-2-(1-cyclopropylethylcarbamoyl)phenylamino)-4-oxoisocrotonate and 250 ml of ethanol, followed by reflux with heating. After stirring for 5.5 hours, the reaction liquid was stood to cool. The precipitated crystals were subjected to suction filtration. The crystals collected after the filtration were washed with ethyl acetate and then with hexane and air dried to obtain 13 g of the desired product.

Example 17

Preparation (4) of 3-bromo-N-(4-chloro-2-(1-cyclopropylethylcarbamoyl)phenyl)-1-(3-chloropyridin-2-yl)-1H-pyrazole-5-carboxamide (1) Preparation of pentyl 2-(3-chloropyridin-2-yl)-5-oxopyrazolidine-3-carboxylate 0.75 g of sodium hydroxide was added to a mixed solution comprising 15 ml of 1-pentanol and 30 ml of toluene, followed by dehydration using an azeotropic dehydrator under reflux with heating, and then toluene was distilled off. Further, 20 ml of toluene was added to the reaction system and then toluene was distilled off with heating again, to obtain a 1-pentanol solution of sodium pentaoxide. 2.5 g of 3-chloro-2-hydrazinylpyridine was added to the reaction liquid at from 70 to 80° C. little by little over a period of 5 minutes, and then 5 ml of 1-pentanol was added, followed by heating at from 70 to 80° C. for 25 minutes. Then, a mixed solution comprising 5.1 g of pentyl maleate and 5 ml of 1-pentanol was dropwise added over a period of 15 minutes, followed by reaction at from 70 to 80° C. further for 2 hours. After the reaction liquid was stood to cool, acetic acid was added to the reaction liquid for neutralization, followed by concentration under reduced pressure. Water was added to the residue, followed by extraction with ethyl acetate, and the organic layer was washed with diluted hydrochloric acid and a sodium chloride aqueous solution and dried over anhydrous sodium sulfate. The solvent was distilled off under reduced pressure, and the residue was purified by silica gel column chromatography (eluent: n-hexane/ethyl acetate=6/4 to 0/1) to obtain 1.29 g of the desired product (melting point: 66 to 68° C.) in the form of brown crystals.

(2) Preparation of pentyl 3-bromo-1-(3-chloropyridin-2-yl)-4,5-dihydro-1H-pyrazole-5-carboxylate A mixed solution comprising 1.2 g of pentyl 2-(3-chloropyridin-2-yl)-5-oxopyrazolidine-3-carboxylate, 0.59 g of phosphorus oxybromide and 18 ml of acetonitrile was gradually heated, and 25 minutes later, the mixed solution was refluxed with heating for one hour. After the reaction liquid was stood to cool, it was slowly added to a saturated sodium hydrogen carbonate aqueous solution, followed by stirring for 5 minutes. The mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=9/1 to 8/2) to obtain 1.06 g of the desired product (melting point: 39 to 42° C.) in the form of pale yellow crystals.

(3) Preparation of pentyl 3-bromo-1-(3-chloropyridin-2-yl)-1H-pyrazole-5-carboxylate 0.5 ml of concentrated sulfuric acid and 1.4 g of potassium peroxodisulfate were added to a mixed solution comprising 1.0 g of pentyl 3-bromo-1-(3-chloropyridin-2-yl)-4,5-dihydro-1H-pyrazole-5-carboxylate and 20 ml of acetonitrile, followed by reflux with heating for 3 hours and 20 minutes. After the reaction liquid was stood to cool, the reaction liquid was slowly added to water, followed by stirring for 15 minutes. The mixed liquid was subjected to extraction with ethyl acetate, and the organic layer was washed with a saturated sodium hydrogen carbonate aqueous solution and a sodium chloride aqueous solution and dried over anhydrous sodium sulfate. The solvent was distilled off under reduced pressure, and the residue was purified by silica gel column chromatography (eluent: n-hexane/ethyl acetate=8.5/1.5 to 8/2) to obtain 0.47 g of the oily desired product.

(4) Preparation of 3-bromo-N-(4-chloro-2-(1-cyclopropylethylcarbamoyl)phenyl)-1-(3-chloropyridin-2-yl)-1H-pyrazole-5-carboxamide 0.11 g potassium tert-butoxide was added to a mixed solution comprising 0.19 g of 2-amino-5-chloro-N-(1-cyclopropylethyl)benzamide, 0.30 g of pentyl 3-bromo-1-(3-chloropyridin-2-yl)-1H-pyrazole-5-carboxylate and 3 ml of dimethyl sulfoxide, followed by reaction at room temperature for 45 minutes. The reaction liquid was slowly added to 40 ml of diluted hydrochloric acid. The mixed liquid was subjected to extraction with ethyl acetate, and the organic layer was washed with a saturated sodium hydrogen carbonate aqueous solution and with a sodium chloride aqueous solution and dried over anhydrous sodium sulfate. The solvent was distilled off under reduced pressure, and the residue was purified by silica gel column chromatography (eluent: n-hexane/ethyl acetate=8/2 to 7.5/2.5) to obtain 0.058 g of the desired product (melting point: 231 to 233° C.) in the form of white crystals.

Example 18

Preparation (2) of 3-bromo-N-[2-bromo-4-chloro-6-[[(1-cyclopropylethyl)amino]carbonyl]phenyl]-1-(3-chloropyridin-2-yl)-1H-pyrazole-5-carboxamide A mixed solution comprising 0.24 g of 3-bromo-N-(4-chloro-2-(1-cyclopropylethylcarbamoyl)phenyl)-1-(3-chloropyridin-2-yl)-1H-pyrazole-5-carboxamide and 5 ml of dimethylformamide was cooled with ice, 46 mg of 60% sodium hydride was added, and the temperature was returned to room temperature, followed by stirring for 25 minutes. The reaction liquid was cooled with ice again, and a mixed solution comprising 0.15 g of bromine and 1 ml of dimethylformamide was dropwise added over a period of 1 minute, followed by reaction at room temperature for 2 hours and 45 minutes. After completion of the reaction, the reaction liquid was slowly added to 60 ml of diluted hydrochloric acid. The mixed liquid was subjected to extraction with ethyl acetate, and the organic layer was washed with a saturated sodium hydrogen carbonate aqueous solution and with a sodium chloride aqueous solution and dried over anhydrous sodium sulfate. The solvent was distilled off under reduced pressure, and the residue was purified by silica gel column chromatography (eluent: n-hexane/ethyl acetate=8/2 to 0/1) to obtain 0.20 g of the desired product (melting point: 244 to 247° C.) in the form of white crystals.

Example 19

Preparation (5) of 3-bromo-N-(4-chloro-2-(1-cyclopropylethylcarbamoyl)phenyl)-1-(3-chloropyridin-2-yl)-1H-pyrazole-5-carboxamide (1) Preparation of phenyl 3-bromo-1-(3-chloropyridin-2-yl)-1H-pyrazole-5-carboxylate 3 ml of thionyl chloride and 5 drops of dimethylformamide were added to a mixed solution comprising 3.0 g of 3-bromo-1-(3-chloropyridin-2-yl)-1H-pyrazole-5-carboxylic acid and 30 ml of toluene, followed by reflux with heating for one hour, and thionyl chloride and toluene were distilled off to obtain crude product of 3-bromo-1-(3-chloropyridin-2-yl)-1H-pyrazole-5-carbonyl chloride.

0.48 g of 60% sodium hydride was added to a mixed solution comprising 1.03 g of phenol and 30 ml of tetrahydrofuran under cooling with ice, followed by reaction at room temperature for 20 minutes, and the mixed liquid was cooled in an ice bath again. To the mixed liquid, a mixed solution comprising the above crude product and 20 ml of toluene was dropwise added under cooling with ice, and the reactor was rinsed with 10 ml of toluene. After reaction under cooling with ice for 15 minutes and at room temperature for one hour, the reaction liquid was slowly added to water. The mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=9.5/0.5 to 7/3) to obtain 2.37 g of the desired product (melting point: 65 to 67° C.) in the form of white crystals.

(2) Preparation of 3-bromo-N-(4-chloro-2-(1-cyclopropylethylcarbamoyl)phenyl)-1-(3-chloropyridin-2-yl)-1H-pyrazole-5-carboxamide 0.18 g of potassium tert-butoxide was added to a mixed solution comprising 0.23 g of 2-amino-5-chloro-N-(1-cyclopropylethyl)benzamide, 0.30 g of phenyl 3-bromo-1-(3-chloropyridin-2-yl)-1H-pyrazole-5-carboxylate and 5 ml of dimethyl sulfoxide, followed by reaction at room temperature for 1 hour. The reaction liquid was slowly added to diluted hydrochloric acid, the mixed liquid was subjected to extraction with ethyl acetate, and the organic layer was washed with a saturated sodium hydrogen carbonate aqueous solution and with a sodium chloride aqueous solution and dried over anhydrous sodium sulfate. The solvent was distilled off under reduced pressure, and the residue was purified by silica gel column chromatography (eluent: n-hexane/ethyl acetate=8/2 to 7.5/2.5) to obtain 0.16 g of the desired product.

Example 20

Preparation (3) of 3-bromo-N-(2-bromo-4-chloro-6-(1-cyclopropylethylcarbamoyl)phenyl)-1-(3-chloropyridin-2-yl)-1H-pyrazole-5-carboxamide 0.45 g of anhydrous sodium sulfate was added to a mixed solution comprising 0.23 g of 2-amino-3-bromo-5-chloro-N-(1-cyclopropylethyl)benzamide, 0.27 g of phenyl 3-bromo-1-(3-chloropyridin-2-yl)-1H-pyrazole-5-carboxylate and 5 ml of dimethyl sulfoxide at room temperature, and 0.16 g of potassium tert-butoxide was added, followed by reaction for one hour. Then, the reaction liquid was slowly added to water. The mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=8/2 to 4/6) to obtain 0.24 g of the desired product.

Example 21

Preparation of phenyl 3-bromo-1-(3-chloropyridin-2-yl)-1H-pyrazole-5-carboxylate (1) Preparation of ethyl 1-(3-chloropyridin-2-yl)-5-fury)-1H-pyrazole-3-carboxylate 7.64 g of 3-chloro-2-hydrazinylpyridine was added to an acetic acid (150 ml) solution comprising 11.19 g of ethyl 2-furoylpyruvate at room temperature, followed by stirring at room temperature further for one hour. Then, the reaction solution was heated to 100° C., followed by reaction for 3 hours. After completion of the reaction, acetic acid was distilled off under reduced pressure, and ethyl acetate and water were added for extraction. The organic layer was washed with (1) a saturated sodium hydrogen carbonate aqueous solution, (2) water and (3) a saturated sodium chloride aqueous solution in this order and then dried over anhydrous magnesium sulfate. The solvent was distilled off under reduced pressure to obtain 14.5 g of crystals of the desired product (melting point: 116.7° C.).

(2) Preparation of 1-(3-chloropyridin-2-yl)-5-fury)-1H-pyrazole-3-carboxylic acid 14.5 g of ethyl 1-(3-chloropyridin-2-yl)-5-furyl-4,5-dihydro-1H-pyrazole-3-carboxylate obtained in the above step (1) was dissolved in a mixed solvent comprising 90 ml of methanol and 45 ml of water, and 2.2 g of sodium hydroxide was added, followed by reaction for 3 hours under reflux. After completion of the reaction, the solvent was distilled off, and water was added to the residue, followed by washing with ethyl ether. The aqueous layer was adjusted to have a pH of 3 by concentrated hydrochloric acid, followed by extraction with ethyl acetate. The organic layer was washed with water and with a saturated sodium chloride aqueous solution and dried over anhydrous magnesium sulfate. The solvent was distilled off under reduced pressure to obtain 11.9 g of crystals of the desired product (melting point: 179.3° C.).

(3) Preparation of 3-N-benzyloxycarbonylamino-1-(3-chloropyridin-2-yl)-5-furyl-1H-pyrazole 11.9 g of 1-(3-chloro-2-pyridyl)-5-furyl-1H-pyrazole-3-carboxylic acid obtained in the above step (2), 4.89 g of benzyl alcohol, 12.4 g of diphenylphosphoryl azide and 5.0 g of triethylamine were added to 100 ml of dioxane, followed by reaction at 90° C. for 3 hours. After completion of the reaction, the solvent was distilled off under reduced pressure, and ethyl acetate and water were added for extraction. The organic layer was washed with (1) 5% hydrochloric acid, (2) a saturated sodium hydrogen carbonate aqueous solution, (3) water and (4) a saturated sodium chloride aqueous solution in this order and dried over anhydrous magnesium sulfate. The solvent was distilled off under reduced pressure, and the residue was purified by silica gel column chromatography (eluent: hexane/ethyl acetate=1/1) to obtain 11.0 g of crystals of the desired product (melting point: 133.4° C.).

(4) Preparation of 3-benzyloxycarbonylamino-1-(3-chloropyridin-2-yl)-1H-5-pyrazolecarboxylic acid 8.9 g of 3-benzyloxycarbonylamino-1-(3-chloropyridin-2-yl)-5-fury)-1H-pyrazole obtained in the above step (3) was dissolved in a mixed solvent comprising 70 ml of acetonitrile and 70 ml of carbon tetrachloride, and an aqueous solution (150 ml) comprising 0.70 g of ruthenium chloride and 21.5 g of sodium periodate was added, followed by stirring at room temperature for 12 hours. After completion of the reaction, the reaction solution was subjected to filtration by celite, the filtrate was concentrated under reduced pressure, and ethyl acetate and 1 N hydrochloric acid were added to the residue for extraction. The organic layer was washed with water and then washed with a saturated sodium hydrogen carbonate aqueous solution, and the aqueous layer was adjusted to have a pH of 3 with concentrated hydrochloric acid, followed by extraction with ethyl acetate. The organic layer was washed with water and with a saturated sodium chloride aqueous solution and dried over anhydrous magnesium sulfate. The solvent was distilled off under reduced pressure to obtain 4.4 g of crystals of the desired product (melting point: 79.1° C.).

(5) Preparation of phenyl 3-benzyloxycarbonylamino-1-(3-chloropyridin-2-yl)-1H-5-pyrazolecarboxylate 2.97 g of 3-benzyloxycarbonylamino-1-(3-chloropyridin-2-yl)-1H-5-pyrazolecarboxylic acid obtained in the above step (4) was dissolved in 30 ml of methylene chloride from which methanol was removed by alumina, and 0.8 ml of oxalyl chloride and one drop of dimethylformamide were added, followed by stirring at room temperature for 30 minutes and reflux for 2 hours. After completion of the reaction, the solvent was distilled off under reduced pressure to obtain 3-benzyloxycarbonylamino-1-(3-chloropyridin-2-yl)-1H-5-pyrazolecarbonyl chloride. A tetrahydrofuran (10 ml) solution of this acid chloride was gradually dropwise added to a suspended solution comprising 0.75 g of phenol and 0.35 g of sodium hydride (60% oil suspension) in tetrahydrofuran (30 ml) under cooling with ice, followed by stirring at room temperature for 8 hours. After completion of the reaction, tetrahydrofuran was distilled off under reduced pressure, ethyl acetate and water were added to the residue for extraction, and the organic layer was washed with water and with a saturated sodium chloride aqueous solution and dried over anhydrous magnesium sulfate. The solvent was distilled off under reduced pressure, and the residue was purified by silica gel column chromatography (eluent: hexane/ethyl acetate=1/1) to obtain 2.8 g of crystals of the desired product (melting point: 150.2° C.).

(6) Preparation of phenyl 3-amino-1-(3-chloropyridin-2-yl)-1H-5-pyrazolecarboxylate 0.6 g of a 10% Pd—C powder was added to an acetic acid (50 ml) solution comprising 3.0 g of phenyl 3-benzyloxycarbonylamino-1-(3-chloropyridin-2-yl)-1H-5-pyrazolecarboxylate obtained by repeatedly carrying out the above step (5), followed by stirring in hydrogen atmosphere at room temperature for 12 hours. The reaction solution was subjected to filtration with celite, and then the filtrate and the liquid obtained after washing the celite were concentrated under reduced pressure. The residue was purified by silica gel column chromatography (eluent: ethyl acetate) to obtain 1.1 g of crystals of the desired product (melting point: 140.4° C.).

(7) Preparation of phenyl 3-bromo-1-(3-chloropyridin-2-yl)-1H-5-pyrazolecarboxylate An acetonitrile (15 ml) solution comprising 1.0 g of phenyl 3-amino-1-(3-chloropyridin-2-yl)-1H-5-pyrazolecarboxylate obtained in the above step (6) was dropwise added to an acetonitrile (20 ml) solution comprising 0.72 g of copper(II) bromide and 0.55 g of t-butyl nitrite (90%) at 0° C., followed by stirring at the same temperature further for 2 hours, and the temperature was gradually returned to room temperature. After completion of the reaction, the reaction solution was concentrated under reduced pressure, and the residue was purified by silica gel column chromatography (eluent: hexane/ethyl acetate=1/1) to obtain 0.88 g of crystals of the desired product (melting point: 64.3° C.).

Example 22

(1) Preparation of benzyl 3-bromo-1-(3-chloropyridin-2-yl)-1H-pyrazole-5-carboxylate 1.5 ml of thionyl chloride and 2 drops of dimethylformamide were added to a mixed solution comprising 1.0 g of 3-bromo-1-(3-chloropyridin-2-yl)-1H-pyrazole-5-carboxylic acid and 10 ml of toluene, followed by reflux with heating for one hour, and thionyl chloride and toluene were distilled off to obtain crude product of 3-bromo-1-(3-chloropyridin-2-yl)-1H-pyrazole-5-carbonyl chloride.

A mixed solution comprising the above crude product and 10 ml of toluene was dropwise added to a mixed solution comprising 0.43 g of benzyl alcohol, 0.40 g of triethylamine and 10 ml of toluene under cooling with ice. After reaction for one hour at room temperature, the reaction liquid was slowly added to water. The mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=7/3) to obtain 1.13 g of the oily desired product.

(2) Preparation of 3-bromo-N-(4-chloro-2-(1-cyclopropylethylcarbamoyl)phenyl-1-(3-chloropyridin-2-yl)-1H-pyrazole-5-carboxamide 0.42 g of anhydrous sodium sulfate was added to a mixed solution comprising 0.12 g of 2-amino-5-chloro-N-(1-cyclopropylethyl)benzamide, 0.20 g of benzyl 3-bromo-1-(3-chloropyridin-2-yl)-1H-pyrazole-5-carboxylate and 5 ml of dimethyl sulfoxide at room temperature, followed by stirring for 5 minutes, and 0.072 g of potassium tert-butoxide was added, followed by reaction at room temperature for 1 hour. Then, the reaction liquid was slowly added to water. The mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=8/2 to 7/3) to obtain 0.050 g of the desired product.

Example 23

Preparation of 4-methoxybenzyl 3-bromo-1-(3-chloropyridin-2-yl)-1H-pyrazole-5-carboxylate 1.52 g of 3-bromo-1-(3-chloropyridin-2-yl)-1H-pyrazole-5-carboxylic acid was dissolved in 10 ml of chloroform, 0.55 ml of thionyl chloride was dropwise added, and 0.05 ml of DMF was added, followed by reflux for 30 minutes. After the reaction liquid was stood to cool, the solvent was distilled off under reduced pressure to obtain crude product of 3-bromo-1-(3-chloropyridin-2-yl)-1H-pyrazole-5-carbonyl chloride. A mixed solution comprising the above crude product and 5 ml of chloroform was dropwise added to a mixed solution comprising 0.85 g of 4-methoxybenzyl alcohol, 1.11 ml of triethylamine and 20 ml of chloroform under cooling with ice, followed by stirring for 5 minutes and reaction at room temperature for 1.5 hours. The reaction solvent was distilled off under reduced pressure, and 50 ml of water was added, followed by extraction with ethyl acetate. The organic layer was washed with a saturated sodium chloride aqueous solution and dried over sodium sulfate. The solvent was distilled off under reduced pressure, and the residue was purified by silica gel column chromatography (eluent: n-hexane/ethyl acetate=1/0 to 3/1) to obtain 1.6 g of the desired product (melting point: 83° C.).

Example 24

(1) Preparation of S-benzyl 3-bromo-1-(3-chloropyridin-2-yl)-1H-pyrazole-5-carbothioate 1.5 ml of thionyl chloride and 2 drops of dimethylformamide were added to a mixed solution comprising 1.5 g of 3-bromo-1-(3-chloropyridin-2-yl)-1H-pyrazole-5-carboxylic acid and 10 ml of toluene, followed by reflux with heating for 1 hour, and thionyl chloride and toluene were distilled off to obtain crude product of 3-bromo-1-(3-chloropyridin-2-yl)-1H-pyrazole-5-carbonyl chloride.
A mixed solution comprising the above crude product and 5 ml of toluene was dropwise added to a mixed solution comprising 0.68 g of benzyl mercaptan, 0.61 g of triethylamine and 20 ml of toluene under cooling with ice. After reaction at room temperature for one hour, the reaction liquid was slowly added to water, the mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=9/1 to 7/3) to obtain 1.65 g of the oily desired product.

(2) Preparation of 3-bromo-N-(4-chloro-2-(1-cyclopropylethylcarbamoyl)phenyl)-1-(3-chloropyridin-2-yl)-1H-pyrazole-5-carboxamide 0.85 g of anhydrous sodium sulfate was added to a mixed solution comprising 0.24 g of 2-amino-5-chloro-N-(1-cyclopropylethyl)benzamide, 0.41 g of S-benzyl 3-bromo-1-(3-chloropyridin-2-yl)-1H-pyrazole-5-carbothioate and 5 ml of dimethyl sulfoxide at room temperature, followed by stirring for 5 minutes, and 0.14 g of potassium tert-butoxide was added, followed by reaction at room temperature for 1 hour. The reaction liquid was slowly added to water, the mixed liquid was subjected to extraction with ethyl acetate, and the organic layer was washed with a sodium chloride aqueous solution and dried over anhydrous sodium sulfate. The solvent was distilled off under reduced pressure, and the residue was purified by silica gel column chromatography (eluent: n-hexane/ethyl acetate=9/1 to 7.5/2.5) to obtain 0.22 g of the desired product.

Example 25

(1) Preparation of S-ethyl 3-bromo-1-(3-chloropyridin-2-yl)-1H-pyrazole-5-carbothioate 1.52 g of 3-bromo-1-(3-chloropyridin-2-yl)-1H-pyrazole-5-carboxylic acid was dissolved in 10 ml of chloroform, 0.55 ml of thionyl chloride was dropwise added, and 0.05 ml of DMF was added, followed by reflux for 30 minutes. After the reaction liquid was stood to cool, the solvent was distilled off under reduced pressure to obtain crude product of 3-bromo-1-(3-chloropyridin-2-yl)-1H-pyrazole-5-carbonyl chloride. Then, a mixed solution comprising the above crude product and 5 ml of toluene was dropwise added to a mixed solution comprising 0.5 ml of ethanethiol, 1.11 ml of triethylamine and 20 ml of chloroform under cooling with ice, followed by stirring for 5 minutes and reaction at room temperature for 14 hours. The reaction solvent was distilled off under reduced pressure, and 50 ml of water was added, followed by extraction with ethyl acetate. The organic layer was washed with a saturated sodium chloride aqueous solution and dried over sodium sulfate. The solvent was distilled off under reduced pressure, and the residue was purified by silica gel column chromatography (eluent: n-hexane/ethyl acetate=1/0 to 3/1) to obtain 1.4 g of the desired product in the form of light red crystals (melting point: 94° C.).

(2) Preparation of 3-bromo-N-(4-chloro-2-(1-cyclopropylethylcarbamoyl)phenyl)-1-(3-chloropyridin-2-yl)-1H-pyrazole-5-carboxamide 0.35 g of S-ethyl 3-bromo-1-(3-chloropyridin-2-yl)-1H-pyrazole-5-carbothioate and 0.24 g of 2-amino-5-chloro-N-(1-cyclopropylethyl)benzamide were dissolved in 5 ml of dimethyl sulfoxide, and 0.85 g of anhydrous sodium sulfate was added, followed by stirring for 5 minutes. 0.14 g of potassium tert-butoxide was added at room temperature, followed by stirring for 1.5 hours. The reaction liquid was added to water, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/1) to obtain 0.24 g of the desired product.

Example 26

Preparation of 1-cyclopropylmethylamine

Method Employing Leuckart Method (1) Preparation of N-(1-cyclopropylethyl)formamide A mixed solution comprising 30 g of 1-cyclopropyl methyl ketone and 66.2 g of formamide was stirred at room temperature, 7.5 g of formic acid was added, and reaction was carried out for 8 hours while 7.5 g of formic acid was added every hour under reflux with heating at 180° C. After completion of the reaction, the reaction mixture was added to water, followed by extraction with ethyl acetate. The organic layer was washed with a saturated sodium chloride aqueous solution and dried over sodium sulfate, and ethyl acetate was distilled off under reduced pressure to obtain crude oily product of N-(1-cyclopropylethyl)formamide.

(2) Preparation of 1-cyclopropylethylamine 115 ml of concentrated hydrochloric acid was added to the crude oily product of N-(1-cyclopropylethyl)formamide obtained in (1), followed by reflux with heating for 1 hour. After the system was cooled, the hydrochloride obtained by distillation under reduced pressure was dissolved in water. The system was cooled with ice, and 1-cyclopropylmethylamine was liberated from the hydrochloride with sodium hydroxide, followed by atmospheric distillation to obtain 20 g of a fraction containing the desired product from the distillate having a boiling point of from 80 to 100° C.

Example 27

Preparation of 1-cyclopropylethylamine

Preparation Using PtO$_2$ 54.7 g of hydroxylammonium chloride was added to 200 ml of an aqueous solution comprising 50 g of cyclopropyl methyl ketone, and 33.6 g of sodium carbonate was gradually added with vigorous stirring, followed by reflux for 4 hours. The reaction liquid was stood to cool, followed by extraction with ether. The organic layer was washed with water and with a saturated sodium chloride aqueous solution and dried over anhydrous sodium sulfate. The solvent was distilled off under reduced pressure to obtain 50 g of crude cyclopropyl methyl ketoxime.

Then, 10 g of the obtained cyclopropyl methyl ketoxime was dissolved in 100 ml of ethyl acetate, 1 g of platinum(IV) oxide was added, and the interior of the reactor was replaced with hydrogen gas, followed by vigorous stirring. After stirring for 16 hours, stirring was terminated, and precipitated platinum was removed by filtration. 10 ml of concentrated hydrochloric acid was added to the supernatant liquid, followed by vigorous shaking in a separating funnel, and both the solvents were distilled off under reduced pressure with heating at 70° C. to obtain 10 g of crude 1-cyclopropylethylamine hydrochloride (purity: 50%).

10 g of the crude 1-cyclopropylethylamine hydrochloride was dissolved in 10 ml of water, and the solution was cooled to 0° C. Sodium hydroxide was slowly added to the solution at 5° C. or below to adjust the pH to 14. A distillating plant equipped with a dry ice condenser was assembled, and 5 g of 1-cyclopropylethylamine having a boiling point of 92 to 94° C. under normal pressure was obtained.

Example 28

Preparation of 2-amino-3-bromo-5-chloro-N-(1-cyclopropylethyl)benzamide (1) Preparation of 5-chloro-N-(1-cyclopropylethyl)-2-nitrobenzamide A mixed liquid comprising 25 g of 5-chloro-2-nitrobenzic acid, 25 ml of toluene, 22.2 g of thionyl chloride and 0.1 ml of dimethylformamide was refluxed with heating for 1 hour to prepare acid chloride. 18.0 g of triethylamine was added to a mixed solution comprising 13.75 g of 1-cyclopropylethylamine and 375 ml of tetrahydrofuran and cooled with ice. The above prepared acid chloride was dissolved in 30 ml of toluene and dropwise added under cooling with ice. After completion of dropwise addition, reaction was carried out at room temperature for 15 hours. After completion of the reaction, the reaction mixture was poured to water, followed by extraction with ethyl acetate. The organic layer was washed with a saturated sodium chloride aqueous solution and dried over sodium sulfate, and ethyl acetate was distilled off under reduced pressure. The residue was purified by silica gel column chromatography to obtain 25 g of the pale yellow desired product (melting point: 137 to 141° C.).

(2) Preparation of 2-amino-5-chloro-N-(1-cyclopropylethyl)benzamide 5.8 g of 5-chloro-N-(1-cyclopropylethyl)-2-nitrobenzamide was dissolved in 88 ml of ethanol, and 12.6 ml of concentrated hydrochloric acid was dropwise added under cooling with ice. After stirring at the same temperature for 0.5 hour, 4.0 g of reduced iron was added dividedly in several addition. After stirring at room temperature for 3 hours, water was added to the reaction mixture, followed by extraction with ethyl acetate. The organic layer was washed with a saturated sodium chloride aqueous solution and dried over sodium sulfate, and ethyl acetate was distilled off under reduced pressure. Hexane/ethyl acetate were added to the residue, followed by stirring, and the mixture was subjected to filtration to obtain 3.5 g of the pale yellow desired product (melting point: 135° C.).

(3) Preparation of 2-amino-3-bromo-5-chloro-N-(1-cyclopropylethyl)benzamide 0.1 g of 2-amino-5-chloro-N-(1-cyclopropylethyl)benzamide was dissolved in 3 ml of N,N-dimethylformamide and cooled to 0° C. 0.02 g of sodium hydride was added, followed by stirring for one hour, and 0.09 g of bromine was added, followed by stirring for 2 hours. The reaction liquid was added to a 1 M-HCl aqueous solution, followed by extraction with ethyl acetate. The organic layer was washed with a saturated sodium chloride aqueous solution and dried over anhydrous sodium sulfate. The solvent was distilled off under reduced pressure, and the residue was purified by silica gel column chromatography (eluent: n-hexane/ethyl acetate=1/0 to 1/1) to obtain 0.08 g of the pale yellow desired produce (melting point: 177° C.).

INDUSTRIAL APPLICABILITY

The present invention provides a novel anthranilamide compound having halogen atoms at specific positions in the benzene ring and the pyrazole ring, having excellent effects as a pesticide in agricultural and horticultural fields, or its salt, and a process for efficiently producing it.

The entire disclosures of Japanese Patent Application No. 2006-339100 filed on Dec. 15, 2006 and Japanese Patent Application No. 2007-152718 filed on Jun. 8, 2007 including specifications, claims and summaries are incorporated herein by reference in their entireties.

The invention claimed is:

1. A process for producing an anthranilamide compound represented by the formula (I) or its salt:

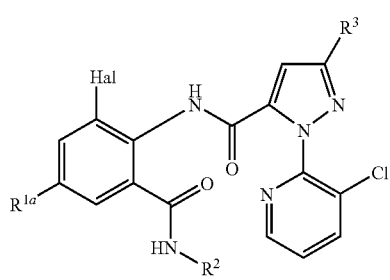

(I)

wherein each of $R^{1a}$ and $R^3$ which are independent of each other, is halogen or haloalkyl; $R^2$ is cyclopropyl alkyl or cyclobutyl alkyl; and Hal is a chlorine atom or a bromine atom, which comprises reacting a compound represented by the formula (II):

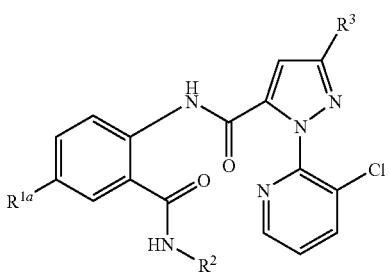

(II)

wherein $R^{1a}$, $R^2$ and $R^3$ are as defined above, with a halogenating agent.

2. A process for producing an anthranilamide compound represented by the formula (I-1) or its salt:

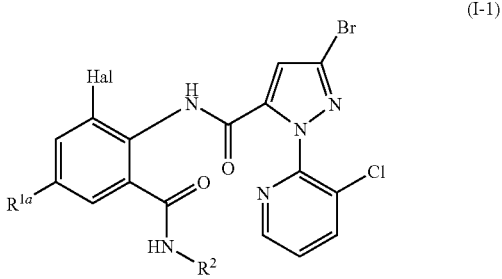

(I-1)

wherein $R^{1a}$ is halogen or haloalkyl; $R^2$ is cyclopropyl alkyl or cyclobutyl alkyl; and Hal is a chlorine atom or a bromine atom, which comprises reacting a compound represented by the formula (II-1):

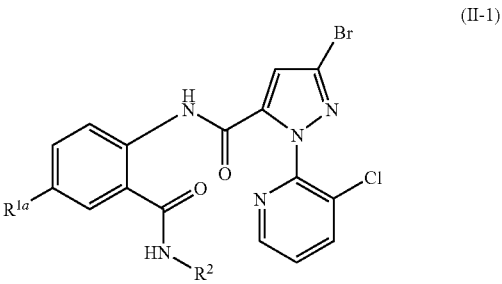

(II-1)

wherein $R^{1a}$ and $R^2$ are as defined above, with a halogenating agent.

3. The process according to claim 2, wherein a compound represented by the formula (II-1):

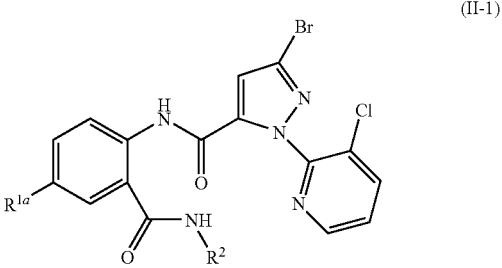

(II-1)

wherein $R^{1a}$ is halogen or haloalkyl; and $R^2$ is cyclopropyl alkyl or cyclobutyl alkyl, obtained by reacting a compound represented by the formula (III-1):

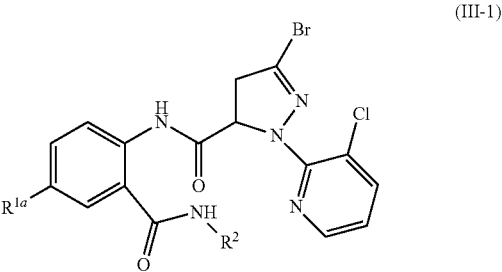

(III-1)

wherein $R^{1a}$ and $R^2$ are as defined above, with an oxidizing agent; or reacting a compound represented by the formula (IV-1):

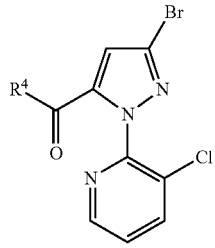

wherein $R^4$ is $C_{5-10}$ alkyloxy, substitutable phenoxy, substitutable benzyloxy, alkylthio, substitutable phenylthio or substitutable benzylthio, with a compound represented by the formula (V-1):

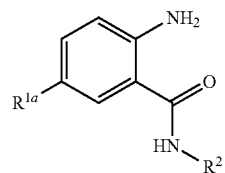

wherein $R^{1a}$ and $R^2$ are as defined above, is reacted with a halogenating agent.

* * * * *